(12) United States Patent
Rahman et al.

(10) Patent No.: US 7,390,613 B1
(45) Date of Patent: Jun. 24, 2008

(54) PHOTOACTIVE COMPOUNDS

(75) Inventors: M. Dalil Rahman, Flemington, NJ (US); David L. Rentkiewicz, Roselle Park, NJ (US)

(73) Assignee: AZ Electronic Materials USA Corp., Somerville, NJ (US)

( * ) Notice: Subject to any disclaimer, the term of this patent is extended or adjusted under 35 U.S.C. 154(b) by 79 days.

(21) Appl. No.: 11/566,309

(22) Filed: Dec. 4, 2006

(51) Int. Cl.
G03F 7/039 (2006.01)
C07C 309/00 (2006.01)
C07D 333/74 (2006.01)

(52) U.S. Cl. ............ 430/270.1; 430/326; 430/914; 430/921; 430/922; 549/14; 549/30; 549/43; 549/44; 549/46; 549/62; 549/83; 562/78

(58) Field of Classification Search ............ 549/14, 549/30, 43, 44, 46, 62, 83; 562/78; 430/270.1, 430/914, 921, 922, 326
See application file for complete search history.

(56) References Cited

U.S. PATENT DOCUMENTS

| | | | |
|---|---|---|---|
| 5,159,088 | A | 10/1992 | Schwalm |
| 5,554,664 | A | 9/1996 | Lamanna et al. |
| 5,874,616 | A | 2/1999 | Howells et al. |
| 5,880,169 | A | 3/1999 | Osawa et al. |
| 6,010,820 | A | 1/2000 | Aoai et al. |
| 6,051,370 | A | 4/2000 | Kim |
| 6,358,665 | B1 | 3/2002 | Pawlowski et al. |
| 6,841,333 | B2 | 1/2005 | Lamanna et al. |
| 6,855,476 | B2 | 2/2005 | Ferreira et al. |
| 6,908,722 | B2 | 6/2005 | Ebata et al. |
| 6,924,323 | B2 | 8/2005 | Ishihara et al. |
| 6,991,888 | B2 | 1/2006 | Padmanaban et al. |
| 7,078,444 | B2 | 7/2006 | Lamanna et al. |
| 2002/0197558 | A1 | 12/2002 | Ferreira et al. |
| 2003/0148211 | A1 | 8/2003 | Kamabuchi et al. |
| 2003/0235782 | A1 | 12/2003 | Padmanaban et al. |
| 2004/0229155 | A1 | 11/2004 | Rahman et al. |
| 2004/0234888 | A1 | 11/2004 | Lamanna et al. |
| 2005/0064340 | A1 | 3/2005 | Aoai |
| 2005/0208420 | A1 | 9/2005 | Ober et al. |

FOREIGN PATENT DOCUMENTS

| | | | |
|---|---|---|---|
| EP | 1 029 767 | A1 | 7/2000 |
| JP | 2003-267949 | A | 9/2003 |
| JP | 2004-359590 | A | 12/2004 |
| WO | WO 02/082185 | A1 | 10/2002 |
| WO | WO 02/082185 | A1 | 12/2002 |

OTHER PUBLICATIONS

Notification Concerning Transmittal of International Preliminary Report on Patentability (Chapter I of the Patent Cooperation Treaty) (Form PCT/IB/326) for PCT/IB2006/001931, which corresponds to related U.S. Appl. No. 11/355,762.
International Preliminary Report on Patentability (Chapter I of the Patent Cooperation Treaty) (Form PCT/TB/373) for PCT/IB2006/001931, which corresponds to related U.S. Appl. No. 11/355,762.
Written Opinion of the Searching Authority (Form PCT/ISA/237) for PCT/IB2006/001931 (attached to Form PCT/IB/326), which corresponds to related U.S. Appl. No. 11/355,762.
English Language Abstract of JP 2003-267949 A.
English Language Abstract of JP 2004-359590 A.
Invitation to Pay Additional Fees and Annex (Form PCT/ISA/206) for PCT/IB2006/001931 (PCT of U.S. Appl. No. 11/355,762).
Notification of Transmittal of the International Search Report and the Written Opinion of the International Searching Authority, or the Declaration (Form PCT/ISA/220) for PCT/IB2006/001931 (PCT of U.S. Appl. No. 11/355,762).
International Search Report (From PCT/ISA/210) for PCT/IB2006/001931 (PCT of U.S. Appl. No. 11/355,762).
Written Opinion of the Searching Authority (Form PCT/ISA/237) for PCT/IB2006/001931 (PCT of U.S. Appl. No. 11/355,762).
Invitation to Pay Additional Fees and Annex (Form PCT/ISA/206) for PCT/IB2006/003315 (PCT of U.S. Appl. No. 11/355,400).
Notification of Transmittal of the International Search Report and the Written Opinion of the International Searching Authority, or the Declaration (Form PCT/ISA/220) for PCT/IB2006/003315 (PCT of U.S. Appl. No. 11/355,400).
International Search Report (From PCT/ISA/210) for PCT/IB2006/003315 (PCT of U.S. Appl. No. 11/355,400).
Written Opinion of the Searching Authority (Form PCT/ISA/237) for PCT/IB2006/003315 (PCT of U.S. Appl. No. 11/355,400).
Jun. 6, 2007 Office Action from related U.S. Appl. No. 11/355,400.
Nov. 1, 2007 Office Action from related U.S. Appl. No. 11/355,400.

*Primary Examiner*—Richard Schilling
(74) *Attorney, Agent, or Firm*—Alan P. Kass

(57) ABSTRACT

The present application relates to a compound of formula Ai Xi Bi where Ai and Bi are each individually an organic onium cation; and Xi is anion of the formula $^-O_3S-CF_2CF_2OCF_2CF_2-SO_3^-$. The compounds are useful as photoactive materials.

20 Claims, No Drawings

PHOTOACTIVE COMPOUNDS

FIELD OF INVENTION

The present invention relates to novel photoactive compounds useful in photoresist compositions in the field of microlithography, and especially useful for imaging negative and positive patterns in the production of semiconductor devices, as well as photoresist compositions and processes for imaging photoresists.

BACKGROUND OF THE INVENTION

Photoresist compositions are used in microlithography processes for making miniaturized electronic components such as in the fabrication of computer chips and integrated circuits. Generally, in these processes, a thin coating of film of a photoresist composition is first applied to a substrate material, such as silicon wafers used for making integrated circuits. The coated substrate is then baked to evaporate any solvent in the photoresist composition and to fix the coating onto the substrate. The photoresist coated on the substrate is next subjected to an image-wise exposure to radiation.

The radiation exposure causes a chemical transformation in the exposed areas of the coated surface. Visible light, ultraviolet (UV) light, electron beam and X-ray radiant energy are radiation types commonly used today in microlithographic processes. After this image-wise exposure, the coated substrate is treated with a developer solution to dissolve and remove either the radiation exposed or the unexposed areas of the photoresist. The trend toward the miniaturization of semiconductor devices has led to the use of new photoresists that are sensitive at lower and lower wavelengths of radiation and has also led to the use of sophisticated multilevel systems to overcome difficulties associated with such miniaturization.

There are two types of photoresist compositions: negative-working and positive-working. The type of photoresist used at a particular point in lithographic processing is determined by the design of the semiconductor device. When negative-working photoresist compositions are exposed image-wise to radiation, the areas of the photoresist composition exposed to the radiation become less soluble to a developer solution (e.g. a cross-linking reaction occurs) while the unexposed areas of the photoresist coating remain relatively soluble to such a solution. Thus, treatment of an exposed negative-working resist with a developer causes removal of the non-exposed areas of the photoresist coating and the creation of a negative image in the coating, thereby uncovering a desired portion of the underlying substrate surface on which the photoresist composition was deposited.

On the other hand, when positive-working photoresist compositions are exposed image-wise to radiation, those areas of the photoresist composition exposed to the radiation become more soluble to the developer solution (e.g. a rearrangement reaction occurs) while those areas not exposed remain relatively insoluble to the developer solution. Thus, treatment of an exposed positive-working photoresist with the developer causes removal of the exposed areas of the coating and the creation of a positive image in the photoresist coating. Again, a desired portion of the underlying surface is uncovered.

Photoresist resolution is defined as the smallest feature, which the resist composition can transfer from the photomask to the substrate with a high degree of image edge acuity after exposure and development. In many leading edge manufacturing applications today, photoresist resolution on the order of less than one-half micron are necessary. In addition, it is almost always desirable that the developed photoresist wall profiles be near vertical relative to the substrate. Such demarcations between developed and undeveloped areas of the resist coating translate into accurate pattern transfer of the mask image onto the substrate. This becomes even more critical as the push toward miniaturization reduces the critical dimensions on the devices. In cases where the photoresist dimensions have been reduced to below 150 nm, the roughness of the photoresist patterns has become a critical issue. Edge roughness, commonly known as line edge roughness, is typically observed for line and space patterns as roughness along the photoresist line, and for contact holes as side wall roughness. Edge roughness can have adverse effects on the lithographic performance of the photoresist, especially in reducing the critical dimension latitude and also in transferring the line edge roughness of the photoresist to the substrate. Hence, photoresists that minimize edge roughness are highly desirable.

Photoresists sensitive to short wavelengths, between about 100 nm and about 300 nm are often used where subhalfmicron geometries are required. Particularly preferred are photoresists comprising non-aromatic polymers, a photoacid generator, optionally a dissolution inhibitor, and solvent.

High resolution, chemically amplified, deep ultraviolet (100-300 nm) positive and negative tone photoresists are available for patterning images with less than quarter micron geometries. To date, there are three major deep ultraviolet (UV) exposure technologies that have provided significant advancement in miniaturization, and these use lasers that emit radiation at 248 nm, 193 nm and 157 nm. Photoresists used in the deep UV typically comprise a polymer which has an acid labile group and which can deprotect in the presence of an acid, a photoactive component which generates an acid upon absorption of light, and a solvent.

Photoresists for 248 nm have typically been based on substituted polyhydroxystyrene and its copolymers, such as those described in U.S. Pat. No. 4,491,628 and U.S. Pat. No. 5,350,660. On the other hand, photoresists for 193 nm exposure require non-aromatic polymers, since aromatics are opaque at this wavelength. U.S. Pat. No. 5,843,624 and GB 2,320,718 disclose photoresists useful for 193 nm exposure. Generally, polymers containing alicyclic hydrocarbons are used for photoresists for exposure below 200 nm. Alicyclic hydrocarbons are incorporated into the polymer for many reasons, primarily since they have relatively high carbon:hydrogen ratios which improve etch resistance, they also provide transparency at low wavelengths and they have relatively high glass transition temperatures. Photoresists sensitive at 157 nm have been based on fluorinated polymers, which are known to be substantially transparent at that wavelength. Photoresists derived from polymers containing fluorinated groups are described in WO 00/67072 and WO 00/17712.

The polymers used in a photoresist are designed to be transparent to the imaging wavelength, but on the other hand, the photoactive component has been typically designed to be absorbing at the imaging wavelength to maximize photosensitivity. The photosensitivity of the photoresist is dependent on the absorption characteristics of the photoactive component, the higher the absorption, the less the energy required to generate the acid, and the more photosensitive is the photoresist.

SUMMARY OF THE INVENTION

The present invention relates to a compound of the formula

Ai Xi Bi, where Ai and Bi are each individually an organic onium cation; and

Xi is anion of the formula $^-O_3S-CF_2CF_2OCF_2CF_2-SO_3^-$, where each of Ai and Bi are selected from

[Structure: dibenzothiophenium cation with substituents $(R_2)_i$, $(R_3)_k$, and $R_1$ on sulfur]

and

Y—Ar where Ar is selected from

[Structure: benzene ring with substituents $R_{1A}$, $R_{2A}$, $R_{3A}$, $R_{4A}$, $R_{5A}$, and a methyl group]

naphthyl, or anthryl;

Y is selected from

[Structures: $R_6-\overset{+}{S}(T)-R_7$; iodonium-substituted phenyl with $R_{1B}, R_{2B}, R_{3B}, R_{4B}, R_{5B}$; $-I^+-$naphtyl; $-I^+-$anthryl]

where $R_1$, $R_2$, $R_3$, $R_{1A}$, $R_{1B}$, $R_{2A}$, $R_{2B}$, $R_{3A}$, $R_{3B}$, $R_{4A}$, $R_{4B}$, $R_{5A}$, and $R_{5B}$ are each independently selected from Z, hydrogen, $OSO_2R_9$, $OR_{20}$, straight or branched alkyl chain optionally containing one or more O atoms, monocycloalkyl or polycycloalkyl group optionally containing one or more O atoms, monocycloalkyl- or polycycloalkylcarbonyl group, aryl, aralkyl, arylcarbonylmethyl group, alkoxyalkyl, alkoxycarbonylalkyl, alkylcarbonyl, monocycloalkyl- or polycycloalkyloxycarbonylalkyl with the cycloalkyl ring optionally containing one or more O atoms, monocycloalkyl- or polycycloalkyloxyalkyl with the cycloalkyl ring optionally containing one or more O atoms, straight or branched perfluoroalkyl, monocycloperfluoroalkyl or polycycloperfluoroalkyl, straight or branched alkoxy chain, nitro, cyano, halogen, carboxyl, hydroxyl, sulfate, tresyl, or hydroxyl; $R_6$ and $R_7$ are each independently selected from straight or branched alkyl chain optionally containing one or more O atoms, monocycloalkyl or polycycloalkyl group optionally containing one or more O atoms, monocycloalkyl- or polycycloalkylcarbonyl group, aryl, aralkyl, straight or branched perfluoroalkyl, monocycloperfluoroalkyl or polycycloperfluoroalkyl, arylcarbonylmethyl group, nitro, cyano, or hydroxyl or $R_6$ and $R_7$ together with the S atom to which they are attached form a 5-, 6-, or 7-membered saturated or unsaturated ring optionally containing one or more O atoms;

$R_9$ is selected from alkyl, fluoroalkyl, perfluoroalkyl, aryl, fluoroaryl, perfluoroaryl, monocycloalkyl or polycycloalkyl group with the cycloalkyl ring optionally containing one or more O atoms, monocyclofluoroalkyl or polycyclofluoroalkyl group with the cycloalkyl ring optionally containing one or more O atoms, or monocycloperfluoralkyl or polycycloperfluoroalkyl group with the cycloalkyl ring optionally containing one or more O atoms;

$R_{20}$ is alkoxyalkyl, alkoxycarbonylalkyl, alkylcarbonyl, monocycloalkyl- or polycycloalkyloxycarbonylalkyl with the cycloalkyl ring optionally containing one or more O atoms, or monocycloalkyl- or polycycloalkyloxyalkyl with the cycloalkyl ring optionally containing one or more O atoms;

T is a direct bond, a divalent straight or branched alkyl group optionally containing one or more O atoms, divalent aryl group, divalent aralkyl group, or divalent monocycloalkyl or polycycloalkyl group optionally containing one or more O atoms;

Z is $-(V)_j-(C(X11)(X12))_n-O-C(=O)-R_8$, where either (i) one of X11 or X12 is straight or branched alkyl chain containing at least one fluorine atom and the other is hydrogen, halogen, or straight or branched alkyl chain or (ii) both of X11 and X12 are straight or branched alkyl chain containing at least one fluorine atom;

V is a linkage group selected from a direct bond, a divalent straight or branched alkyl group optionally containing one or more O atoms, divalent aryl group, divalent aralkyl group, or divalent monocycloalkyl or polycycloalkyl group optionally containing one or more O atoms;

X2 is hydrogen, halogen, or straight or branched alkyl chain optionally containing one or more O atoms;

$R_8$ is a straight or branched alkyl chain optionally containing one or more O atoms, a monocycloalkyl or polycycloalkyl group optionally containing one or more O atoms, or aryl;

X3 is hydrogen, straight or branched alkyl chain, halogen, cyano, or $-C(=O)-R_{50}$ where $R_{50}$ is selected from straight or branched alkyl chain optionally containing one or more O atoms or $-O-R_{51}$ where $R_{51}$ is hydrogen or straight or branched alkyl chain;

each of i and k are independently 0 or a positive integer;

j is 0 to 10;

m is 0 to 10;

and n is 0 to 10, the straight or branched alkyl chain optionally containing one or more O atoms, straight or branched alkyl chain, straight or branched alkoxy chain, monocycloalkyl or polycycloalkyl group optionally containing one or more O atoms, monocycloalkyl- or polycycloalkylcarbonyl group, alkoxyalkyl, alkoxycarbonylalkyl, alkylcarbonyl, monocycloalkyl- or polycycloalkyloxycarbonylalkyl with the cycloalkyl ring optionally containing one or more O atoms, monocycloalkyl- or polycycloalkyloxyalkyl with the cycloalkyl ring optionally containing one or more O atoms, aralkyl, aryl, naphthyl, anthryl, 5-, 6-, or 7-membered saturated or unsaturated ring optionally containing one or more O atoms, or arylcarbonylmethyl group being unsubstituted or substituted by one or more groups selected from the group consisting of Z, halogen, alkyl, $C_{1-8}$ perfluoroalkyl, monocycloalkyl or polycycloalkyl, $OR_{20}$, alkoxy, $C_{3-20}$ cyclic alkoxy, dialkylamino, dicyclic dialkylamino, hydroxyl, cyano, nitro, tresyl, oxo, aryl, aralkyl, oxygen atom, $CF_3SO_3$, aryloxy, arylthio, and groups of formulae (II) to (VI):

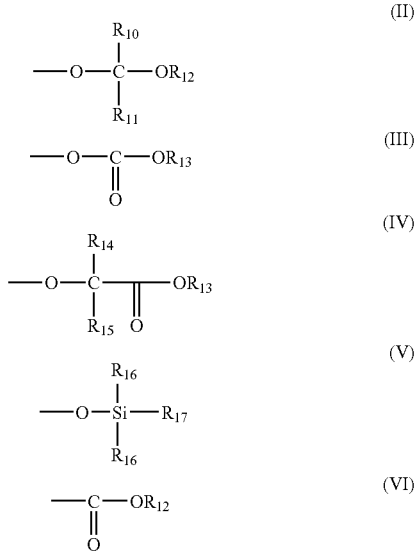

wherein $R_{10}$ and $R_{11}$ each independently represent a hydrogen atom, a straight or branched alkyl chain optionally containing one or more O atoms, or a monocycloalkyl or polycycloalkyl group optionally containing one or more O atoms, or $R_{10}$ and $R_{11}$ together can represent an alkylene group to form a five- or six-membered ring;

$R_{12}$ represents a straight or branched alkyl chain optionally containing one or more O atoms, a monocycloalkyl or polycycloalkyl group optionally containing one or more O atoms, or aralkyl, or $R_{10}$ and $R_{12}$ together represent an alkylene group which forms a five- or six-membered ring together with the interposing —C—O— group, the carbon atom in the ring being optionally substituted by an oxygen atom;

$R_{13}$ represents a straight or branched alkyl chain optionally containing one or more O atoms or a monocycloalkyl or polycycloalkyl group optionally containing one or more O atoms;

$R_{14}$ and $R_{15}$ each independently represent a hydrogen atom, a straight or branched alkyl chain optionally containing one or more O atoms or a monocycloalkyl or polycycloalkyl group optionally containing one or more O atoms;

$R_{16}$ represents a straight or branched alkyl chain optionally containing one or more O atoms, a monocycloalkyl or polycycloalkyl group optionally containing one or more O atoms, aryl, or aralkyl; and $R_{17}$ represents straight or branched alkyl chain optionally containing one or more O atoms, a monocycloalkyl or polycycloalkyl group optionally containing one or more O atoms, aryl, aralkyl, the group —Si$(R_{16})_2R_{17}$, or the group —O—Si$(R_{16})_2R_{17}$, the straight or branched alkyl chain optionally containing one or more O atoms, monocycloalkyl or polycycloalkyl group optionally containing one or more O atoms, aryl, and aralkyl being unsubstituted or substituted as above.

The present invention also relates to a photoresist composition comprising a polymer containing an acid labile group and a compound as described above together with one or more additional photoacid generators selected from (a) a compound having the formula Ai Xi1 Bi, where Ai and Bi are as defined above and Xi1 is an anion of the formula Q—$R_{500}$—$SO_3^-$, where Q is selected from $^-O_3S$ and $^-O_2C$; and $R_{500}$ is a group selected from linear or branched alkyl, cycloalkyl, aryl, or combinations thereof, optionally containing a catenary S or N, where the alkyl, cycloalkyl, and aryl groups are unsubstituted or substituted by one or more groups selected from the group consisting of halogen, unsubstituted or substituted alkyl, unsubstituted or substituted $C_{1-8}$ perfluoroalkyl, hydroxyl, cyano, sulfate, and nitro; and (b) a compound having the formula Ai Xi2, where Ai is an organic onium cation as previously defined and Xi2 is an anion; and mixtures of (a) and (b) thereof. Examples of the Xi2 anion include $CF_3SO_3^-$, $CHF_2SO_3^-$, $CH_3SO_3^-$, $CCl_3SO_3^-$, $C_2F_5SO_3^-$, $C_2HF_4SO_3^-$, $C_4F_9SO_3^-$, camphor sulfonate, perfluorooctane sulfonate, benzene sulfonate, pentafluorobenzene sulfonate, toluene sulfonate, perfluorotoluene sulfonate, $(Rf1SO_2)_3C^-$ and $(Rf1SO_2)_2N^-$, wherein each Rf1 is independently selected from the group consisting of highly fluorinated or perfluorinated alkyl or fluorinated aryl radicals and may be cyclic, when a combination of any two Rf1 groups are linked to form a bridge, further, the Rf1 alkyl chains contain from 1-20 carbon atoms and may be straight, branched, or cyclic, such that divalent oxygen, trivalent nitrogen or hexavalent sulfur may interrupt the skeletal chain, further when Rf1 contains a cyclic structure, such structure has 5 or 6 ring members, optionally, 1 or 2 of which are heteroatoms, and Rg—O—Rf2—$SO_3^-$, where Rf2 is selected from the group consisting of linear or branched $(CF_2)_j$ where j is an integer from 4 to 10 and $C_1$-$C_{12}$ cycloperfluoroalkyl divalent radical which is optionally perfluoro$C_{1-10}$alkyl substituted, Rg is selected from the group consisting of $C_1$-$C_{20}$ linear, branched, monocycloalkyl or polycycloalkyl, $C_1$-$C_{20}$ linear, branched, monocycloalkenyl or polycycloalkenyl, aryl, and aralkyl, the alkyl, alkenyl, aralkyl and aryl groups being unsubstituted, substituted, optionally containing one or more catenary oxygen atoms, partially fluorinated or perfluorinated. Examples of such anions Xi1 include $(C_2F_5SO_2)_2N^-$, $(C_4F_9SO_2)_2N^-$, $(C_8F_{17}SO_2)_3C^-$, $(CF_3SO_2)_3C^-$, $(CF_3SO_2)_2N^-$, $(CF_3SO_2)_2(C_4F_9SO_2)C^-$, $(C_2F_5SO_2)_3C^-$, $(C_4F_9SO_2)_3C^-$, $(CF_3SO_2)_2(C_2F_5SO_2)C^-$, $(C_4F_9SO_2)(C_2F_5SO_2)_2C^-$, $(CF_3SO_2)(C_4F_9SO_2)N^-$, $[(CF_3)_2NC_2F_4SO_2]_2N^-$, $(CF_3)_2NC_2F_4SO_2C^-$ $(SO_2CF_3)_2$, $(3,5$-bis$(CF_3)C_6H_3)SO_2N$—$SO_2CF_3$, $C_6F_5SO_2C^-(SO_2CF_3)_2$, $C_6F_5SO_2N^-SO_2CF_3$,

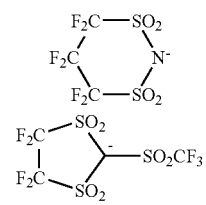

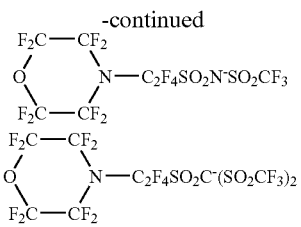

CF$_3$CHFO(CF$_2$)$_4$SO$_3^-$, CF$_3$CH$_2$O(CF$_2$)$_4$SO$_3^-$, CH$_3$CH$_2$O(CF$_2$)$_4$SO$_3$, CH$_3$CH$_2$CH$_2$O(CF$_2$)$_4$SO$_3^-$, CH$_3$O(CF$_2$)$_4$SO$_3$, C$_2$H$_5$O(CF$_2$)$_4$SO$_3$, C$_4$H$_9$O(CF$_2$)$_4$SO$_3^-$, C$_6$H$_5$CH$_2$O(CF$_2$)$_4$SO$_3^-$, C$_2$H$_5$OCF$_2$CF(CF$_3$)SO$_3^-$, CH$_2$=CHCH$_2$O(CF$_2$)$_4$SO$_3$, CH$_3$OCF$_2$CF(CF$_3$)SO$_3^-$, C$_4$H$_9$OCF$_2$CF(CF$_3$)SO$_3^-$, C$_8$H$_{17}$O(CF$_2$)$_2$SO$_3^-$, and C$_4$H$_9$O(CF$_2$)$_2$SO$_3^-$. Other examples of suitable anions can be found in U.S. Pat. No. 6,841,333 and U.S. Pat. No. 5,874,616.

Examples of Ai Xi2 include bis(4-t-butylphenyl) iodonium bis-perfluoroethane sulfonimide, diphenyliodonium trifluoromethane sulfonate, diphenyliodonium nonafluorobutane sulfonate, triphenylsulfonium trifluoromethane sulfonate, triphenylsulfonium nonafluorobutane sulfonate, 4-(1-butoxyphenyl)diphenylsulfonium bis-(perfluorobutanesulfonyl)imide, 4-(1-butoxyphenyl)diphenylsulfonium bis-(perfluoroethanesulfonyl)imide, 2,4,6-trimethylphenyldiphenylsulfonium bis-perfluorobutanesulfonyl)imide, 2,4,6-trimethylphenyldiphenylsulfonium bis-(perfluoroethanesulfonyl)imide, toluenediphenylsulfonium bis-(perfluorobutanesulfonyl)imide, toluenediphenylsulfonium bis-(perfluoroethanesulfonyl)imide, toluenediphenylsulfonium-(trifluoromethyl perfluorobutylsulfonyl)imide, tris-(tert-butylphenyl)sulfonium-(trifluoromethyl perfluorobutylsulfonyl)imide, tris-(tert-butylphenyl)sulfonium bis-(perfluorobutanesulfonyl)imide, tris-(tert-butylphenyl)sulfonium-bis-(trifluoromethanesulfonyl)imide, and the like as well as other photoacid generators known to those skilled in the art.

The ratio of the inventive photoacid generators of the present application to the additional photoacid generators Ai Xi1 Bi, Ai Xi2, and mixtures thereof can range from about 1:1 to about 1:4, and further from about 1:1.25 to about 1:3.5.

DETAILED DESCRIPTION OF THE INVENTION

The present invention relates to a compound of the formula

Ai Xi Bi, where Ai and Bi are each individually an organic onium cation; and

Xi is anion of the formula $^-$O$_3$S—CF$_2$CF$_2$OCF$_2$CF$_2$—SO$_3^-$, where each of Ai and Bi are selected from

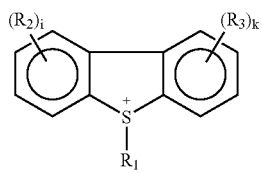

and

Y—Ar where Ar is selected from

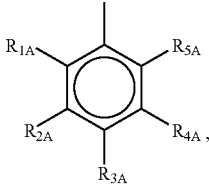

naphthyl, or anthryl;

Y is selected from

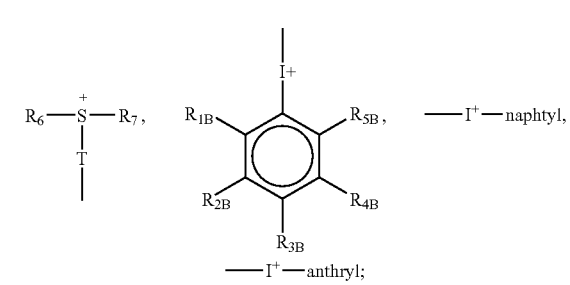

where $R_1$, $R_2$, $R_3$, $R_{1A}$, $R_{1B}$, $R_{2A}$, $R_{2B}$, $R_{3A}$, $R_{3B}$, $R_{4A}$, $R_{4B}$, $R_{5A}$, and $R_{5B}$ are each independently selected from Z, hydrogen, OSO$_2$R$_9$, OR$_{20}$, straight or branched alkyl chain optionally containing one or more O atoms, monocycloalkyl or polycycloalkyl group optionally containing one or more O atoms, monocycloalkyl- or polycycloalkylcarbonyl group, aryl, aralkyl, arylcarbonylmethyl group, alkoxyalkyl, alkoxycarbonylalkyl, alkylcarbonyl, monocycloalkyl- or polycycloalkyloxycarbonylalkyl with the cycloalkyl ring optionally containing one or more O atoms, monocycloalkyl- or polycycloalkyloxyalkyl with the cycloalkyl ring optionally containing one or more O atoms, straight or branched perfluoroalkyl, monocycloperfluoroalkyl or polycycloperfluoroalkyl, straight or branched alkoxy chain, nitro, cyano, halogen, carboxyl, hydroxyl, sulfate, tresyl, or hydroxyl;

$R_6$ and $R_7$ are each independently selected from straight or branched alkyl chain optionally containing one or more O atoms, monocycloalkyl or polycycloalkyl group optionally containing one or more O atoms, monocycloalkyl- or polycycloalkylcarbonyl group, aryl, aralkyl, straight or branched perfluoroalkyl, monocycloperfluoroalkyl or polycycloperfluoroalkyl, arylcarbonylmethyl group, nitro, cyano, or hydroxyl or $R_6$ and $R_7$ together with the S atom to which they are attached form a 5-, 6-, or 7-membered saturated or unsaturated ring optionally containing one or more O atoms;

$R_9$ is selected from alkyl, fluoroalkyl, perfluoroalkyl, aryl, fluoroaryl, perfluoroaryl, monocycloalkyl or polycycloalkyl group with the cycloalkyl ring optionally containing one or more O atoms, monocyclofluoroalkyl or polycyclofluoroalkyl group with the cycloalkyl ring optionally containing one or more O atoms, or monocycloperfluoralkyl or polycycloperfluoroalkyl group with the cycloalkyl ring optionally containing one or more O atoms;

$R_{20}$ is alkoxyalkyl, alkoxycarbonylalkyl, alkylcarbonyl, monocycloalkyl- or polycycloalkyloxycarbonylalkyl with the cycloalkyl ring optionally containing one or more O atoms, or monocycloalkyl- or polycycloalkyloxyalkyl with the cycloalkyl ring optionally containing one or more O atoms;

T is a direct bond, a divalent straight or branched alkyl group optionally containing one or more O atoms, divalent aryl group, divalent aralkyl group, or divalent monocycloalkyl or polycycloalkyl group optionally containing one or more O atoms; Z is $-(V)_j-(C(X11)(X12))_n-O-C(=O)-R_8$, where either (i) one of X11 or X12 is straight or branched alkyl chain containing at least one fluorine atom and the other is hydrogen, halogen, or straight or branched alkyl chain or (ii) both of X11 and X12 are straight or branched alkyl chain containing at least one fluorine atom;

V is a linkage group selected from a direct bond, a divalent straight or branched alkyl group optionally containing one or more O atoms, divalent aryl group, divalent aralkyl group, or divalent monocycloalkyl or polycycloalkyl group optionally containing one or more O atoms;

X2 is hydrogen, halogen, or straight or branched alkyl chain optionally containing one or more O atoms;

$R_8$ is a straight or branched alkyl chain optionally containing one or more O atoms, a monocycloalkyl or polycycloalkyl group optionally containing one or more O atoms, or aryl;

X3 is hydrogen, straight or branched alkyl chain, halogen, cyano, or $-C(=O)-R_{50}$ where $R_{50}$ is selected from straight or branched alkyl chain optionally containing one or more O atoms or $-O-R_{51}$ where $R_{51}$ is hydrogen or straight or branched alkyl chain;

each of i and k are independently 0 or a positive integer;

j is 0 to 10;

m is 0 to 10;

and n is 0 to 10, the straight or branched alkyl chain optionally containing one or more O atoms, straight or branched alkyl chain, straight or branched alkoxy chain, monocycloalkyl or polycycloalkyl group optionally containing one or more O atoms, monocycloalkyl- or polycycloalkylcarbonyl group, alkoxyalkyl, alkoxycarbonylalkyl, alkylcarbonyl, monocycloalkyl- or polycycloalkyloxycarbonylalkyl with the cycloalkyl ring optionally containing one or more O atoms, monocycloalkyl- or polycycloalkyloxyalkyl with the cycloalkyl ring optionally containing one or more O atoms, aralkyl, aryl, naphthyl, anthryl, 5-, 6-, or 7-membered saturated or unsaturated ring optionally containing one or more O atoms, or arylcarbonylmethyl group being unsubstituted or substituted by one or more groups selected from the group consisting of Z, halogen, alkyl, $C_{1-8}$ perfluoroalkyl, monocycloalkyl or polycycloalkyl, $OR_{20}$, alkoxy, $C_{3-20}$ cyclic alkoxy, dialkylamino, dicyclic dialkylamino, hydroxyl, cyano, nitro, tresyl, oxo, aryl, aralkyl, oxygen atom, $CF_3SO_3$, aryloxy, arylthio, and groups of formulae (II) to (VI):

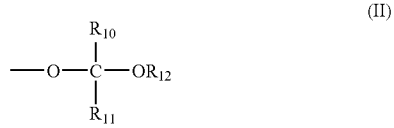

(II)

-continued

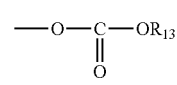

(III)

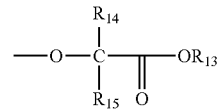

(IV)

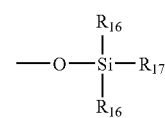

(V)

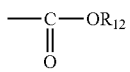

(VI)

wherein $R_{10}$ and $R_{11}$ each independently represent a hydrogen atom, a straight or branched alkyl chain optionally containing one or more O atoms, or a monocycloalkyl or polycycloalkyl group optionally containing one or more O atoms, or $R_{10}$ and $R_{11}$ together can represent an alkylene group to form a five- or six-membered ring;

$R_{12}$ represents a straight or branched alkyl chain optionally containing one or more O atoms, a monocycloalkyl or polycycloalkyl group optionally containing one or more O atoms, or aralkyl, or $R_{10}$ and $R_{12}$ together represent an alkylene group which forms a five- or six-membered ring together with the interposing $-C-O-$ group, the carbon atom in the ring being optionally substituted by an oxygen atom;

$R_{13}$ represents a straight or branched alkyl chain optionally containing one or more O atoms or a monocycloalkyl or polycycloalkyl group optionally containing one or more O atoms;

$R_{14}$ and $R_{15}$ each independently represent a hydrogen atom, a straight or branched alkyl chain optionally containing one or more O atoms or a monocycloalkyl or polycycloalkyl group optionally containing one or more O atoms;

$R_{16}$ represents a straight or branched alkyl chain optionally containing one or more O atoms, a monocycloalkyl or polycycloalkyl group optionally containing one or more O atoms, aryl, or aralkyl; and $R_{17}$ represents straight or branched alkyl chain optionally containing one or more O atoms, a monocycloalkyl or polycycloalkyl group optionally containing one or more O atoms, aryl, aralkyl, the group $-Si(R_{16})_2R_{17}$, or the group $-O-Si(R_{16})_2R_{17}$, the straight or branched alkyl chain optionally containing one or more O atoms, monocycloalkyl or polycycloalkyl group optionally containing one or more O atoms, aryl, and aralkyl being unsubstituted or substituted as above.

The present invention also relates to a photoresist composition comprising a polymer containing an acid labile group and a compound as described above together with one or more additional photoacid generators selected from (a) a compound having the formula Ai Xi1 Bi, where Ai and Bi are as defined above and Xi1 is an anion of the formula $Q-R_{500}-SO_3^-$, where Q is selected from $^-O_3S$ and $^-O_2C$; and $R_{500}$ is a group selected from linear or branched alkyl, cycloalkyl, aryl, or combinations thereof, optionally containing a catenary S or N, where the alkyl, cycloalkyl, and aryl groups are unsubstituted or substituted by one or more groups selected from the group consisting of halogen, unsubstituted or substituted alkyl, unsubstituted or substituted $C_{1-8}$ perfluoroalkyl, hydroxyl, cyano, sulfate, and nitro; and (b) a compound having the formula Ai Xi2, where Ai is an organic onium cation as previously defined and Xi2 is an anion; and mixtures of (a) and (b) thereof. Examples of the Xi2 anion include $CF_3SO_3^-$, $CHF_2SO_3^-$, $CH_3SO_3^-$, $CCl_3SO_3^-$, $C_2F_5SO_3^-$, $C_2HF_4SO_3^-$, $C_4F_9SO_3$, camphor sulfonate, perfluorooctane sulfonate, benzene sulfonate, pentafluorobenzene sulfonate, toluene sulfonate, perfluorotoluene sulfonate, $(RflSO_2)_3C^-$ and $(Rf1SO_2)_2N^-$, wherein each Rf1 is independently selected from the group consisting of highly fluorinated or perfluorinated alkyl or fluorinated aryl radicals and may be cyclic, when a combination of any two Rf1 groups are linked to form a bridge, further, the Rf1 alkyl chains contain from 1-20 carbon atoms and may be straight, branched, or cyclic, such that divalent oxygen, trivalent nitrogen or hexavalent sulfur may interrupt the skeletal chain, further when Rf1 contains a cyclic structure, such structure has 5 or 6 ring members, optionally, 1 or 2 of which are heteroatoms, and Rg—O—Rf2—$SO_3^-$, where Rf2 is selected from the group consisting of linear or branched $(CF_2)_j$ where j is an integer from 4 to 10 and $C_1$-$C_{12}$ cycloperfluoroalkyl divalent radical which is optionally perfluoro$C_{1-10}$alkyl substituted, Rg is selected from the group consisting of $C_1$-$C_{20}$ linear, branched, monocycloalkyl or polycycloalkyl, $C_1$-$C_{20}$ linear, branched, monocycloalkenyl or polycycloalkenyl, aryl, and aralkyl, the alkyl, alkenyl, aralkyl and aryl groups being unsubstituted, substituted, optionally containing one or more catenary oxygen atoms, partially fluorinated or perfluorinated. Examples of such anions Xi1 include $(C_2F_5SO_2)_2N^-$, $(C_4F_9SO_2)_2N^-$, $(C_8F_{17}SO_2)_3C^-$, $(CF_3SO_2)_3C^-$, $(CF_3SO_2)_2N^-$, $(CF_3SO_2)_2(C_4F_9SO_2)C^-$, $(C_2F_5SO_2)_3C^-$, $(C_4F_9SO_2)_3C^-$, $(CF_3SO_2)_2(C_2F_5SO_2)C^-$, $(C_4F_9SO_2)(C_2F_5SO_2)_2C^-$, $(CF_3SO_2)_2(C_4F_9SO_2)N^-$, $[(CF_3)_2NC_2F_4SO_2]_2N^-$, $(CF_3)_2NC_2F_4SO_2C^-(SO_2CF_3)_2$, $(3,5\text{-bis}(CF_3)C_6H_3)SO_2N^-SO_2CF_3$, $C_6F_5SO_2C^-(SO_2CF_3)_2$, $C_6F_5SO_2N^-SO_2CF_3$,

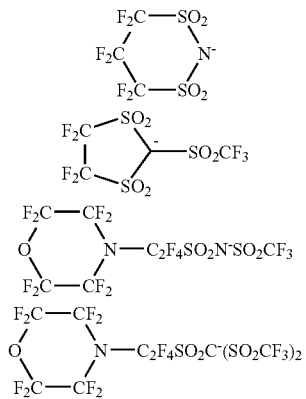

$CF_3CHFO(CF_2)_4SO_3^-$, $CF_3CH_2O(CF_2)_4SO_3^-$, $CH_3CH_2O(CF_2)_4SO_3$, $CH_3CH_2CH_2O(CF_2)_4SO_3^-$, $CH_3O(CF_2)_4SO_3^-$, $C_2H_5O(CF_2)_4SO_3$, $C_4H_9O(CF_2)_4SO_3^-$, $C_6H_5CH_2O(CF_2)_4SO_3^-$, $C_2H_5OCF_2CF(CF_3)SO_3^-$, $CH_2=CHCH_2O(CF_2)_4O_3$, $CH_3OCF_2CF(CF_3)SO_3^-$, $C_4H_9OCF_2CF(CF_3)SO_3^-$, $C_8H_{17}O(CF_2)_2SO_3^-$, and $C_4H_9O(CF_2)_2SO_3^-$. Other examples of suitable anions can be found in U.S. Pat. No. 6,841,333 and U.S. Pat. No. 5,874,616.

Examples of Ai Xi2 include bis(4-t-butylphenyl) iodonium bis-perfluoroethane sulfonimide, diphenyliodonium trifluoromethane sulfonate, diphenyliodonium nonafluorobutane sulfonate, triphenylsulfonium trifluoromethane sulfonate, triphenylsulfonium nonafluorobutane sulfonate, 4-(1-butoxyphenyl)diphenylsulfonium bis-(perfluorobutanesulfonyl) imide, 4-(1-butoxyphenyl)diphenylsulfonium bis-(perfluoroethanesulfonyl)imide, 2,4,6-trimethylphenyldiphenylsulfonium bis-perfluorobutanesulfonyl)imide, 2,4,6-trimethylphenyldiphenylsulfonium bis-(perfluoroethanesulfonyl)imide, toluenediphenylsulfonium bis-(perfluorobutanesulfonyl)imide, toluenediphenylsulfonium bis-(perfluoroethanesulfonyl)imide, toluenediphenylsulfonium-(trifluoromethyl perfluorobutylsulfonyl)imide, tris-(tert-butylphenyl)sulfonium-(trifluoromethyl perfluorobutylsulfonyl)imide, tris-(tert-butylphenyl)sulfonium bis-(perfluorobutanesulfonyl)imide, tris-(tert-butylphenyl)sulfonium-bis-(trifluoromethanesulfonyl)imide, and the like as well as other photoacid generators known to those skilled in the art.

The term alkyl as used herein means a straight or branched chain hydrocarbon. Representative examples of alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, and n-decyl.

Alkylene refers to divalent alkyl radicals, which can be linear or branched, such as, for example, methylene, ethylene, propylene, butylene or the like.

By the term aryl is meant a radical derived from an aromatic hydrocarbon by the elimination of one atom of hydrogen and can be substituted or unsubstituted. The aromatic hydrocarbon can be mononuclear or polynuclear. Examples of aryl of the mononuclear type include phenyl, tolyl, xylyl, mesityl, cumenyl, and the like. Examples of aryl of the polynuclear type include naphthyl, anthryl, phenanthryl, and the like. The aryl group can be unsubstituted or substituted as provided for hereinabove.

The term alkoxy refers to a group of alkyl-O—, where alkyl is defined herein. Representative examples of alkoxy include, but are not limited to, methoxy, ethoxy, propoxy, 2-propoxy, butoxy, tert-butoxy, pentyloxy, and hexyloxy.

The term aryloxy refers to a group of aryl-O—, where aryl is defined herein.

By the term aralkyl is meant an alkyl group containing an aryl group. It is a hydrocarbon group having both aromatic and aliphatic structures, that is, a hydrocarbon group in which a lower alkyl hydrogen atom is substituted by a mononuclear or polynuclear aryl group. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, naphthylmethyl, and the like.

The term monocycloalkyl as used herein, refers to an optionally substituted, saturated or partially unsaturated monocycloalkyl ring system, where if the ring is partially unsaturated, it is then a monocycloalkenyl group. The term polycycloalkyl as used herein refers to an optionally substituted, saturated or partially unsaturated polycycloalkyl ring system containing two or more rings, where if the ring is partially unsaturated, it is then a polycycloalkenyl group. Examples of monocycloalkyl or polycycloalkyl groups optionally containing one or more O atoms are well know to those skilled in the art and include, for example, cyclopropyl, cyclobutyl, cyclopentyl, cycloheptyl, cyclohexyl, 2-methyl-2-norbornyl, 2-ethyl-2-norbornyl, 2-methyl-2-isobornyl, 2-ethyl-2-isobornyl, 2-methyl-2-adamantyl, 2-ethyl-2-adamantyl, 1-adamantyl-1-methylethyl, adamantyl, tricyclodecyl, 3-oxatricyclo[4.2.1.0$^{2,5}$]nonyl, tetracyclododecanyl, tetracyclo [5.2.2.0.0] undecanyl, bornyl, isobornyl norbornyl lactone, adamantyl lactone and the like.

The term alkoxycarbonylalkyl embraces alkyl radicals substituted with an alkoxycarbonyl radical as defined herein. Examples of alkoxycarbonylalkyl radicals include methoxycarbonyl methyl [CH$_3$O—C(=O)—CH$_2$—], ethoxycarbonyl methyl [CH$_3$CH$_2$O—C(=O)—CH$_2$—], methoxycarbonylethyl [CH$_3$O—C(=O)—CH$_2$CH$_2$—], and ethoxycarbonylethyl [CH$_3$CH$_2$O—C(=O)—CH$_2$CH$_2$—].

The term alkylcarbonyl as used herein means an alkyl group, as defined herein, appended to the parent molecular moiety through a carbonyl group, as defined herein, which can be generically represented as alkyl-C(O)—. Representative examples of alkylcarbonyl include, but are not limited to acetyl (methyl carbonyl), butyryl (propylcarbonyl), octanoyl (heptylcarbonyl), dodecanoyl (undecylcarbonyl), and the like.

Alkoxycarbonyl means alkyl-O—C(O)—, wherein alkyl is as previously described. Non-limiting examples include methoxycarbonyl [CH$_3$O—C(O)—] and the ethoxycarbonyl [CH$_3$CH$_2$O—C(O)—], benzyloxycarbonyl [C$_6$H$_5$CH$_2$O—C(O)—] and the like.

Alkoxyalkyl means that a terminal alkyl group is linked through an ether oxygen atom to an alkyl moiety, which can be generically represented as alkyl-O-alkyl wherein the alkyl groups can be linear or branched. Examples of alkoxyalkyl include, but are not limited to, methoxypropyl, methoxybutyl, ethoxypropyl, methoxymethyl Monocycloalkyl- or polycycloalkyloxycarbonylalkyl means that a terminal monocycloalkyl or polycycloalkyl group is linked through —O—C(=O)— to an alkyl moiety, generically represented as monocycloalkyl- or polycycloalkyl-O—C(=O)-alkyl.

Monocycloalkyl- or polycycloalkyloxyalkyl means that a terminal monocycloalkyl or polycycloalkyl group is linked through an ether oxygen atom to an alkyl moiety, which can be generically represented as monocycloalkyl- or polycycloalkyl-O-alkyl.

Monocyclofluoroalkyl- or polycyclofluoroalkyl means a monocyclalkyl- or polycycloalkyl group substituted with one or more fluorine atoms.

Polymers useful in the photoresist compositions include those that have acid labile groups that make the polymer insoluble in aqueous alkaline solution, but such a polymer in the presence of an acid catalytically deprotects the polymer, wherein the polymer then becomes soluble in an aqueous alkaline solution. The polymers preferably are transparent below 200 nm, and are essentially non-aromatic, and preferably are acrylates and/or cycloolefin polymers. Such polymers are, for example, but not limited to, those described in U.S. Pat. No. 5,843,624, U.S. Pat. No. 5,879,857, WO 97/33, 198, EP 789,278 and GB 2,332,679. Nonaromatic polymers that are preferred for irradiation below 200 nm are substituted acrylates, cycloolefins, substituted polyethylenes, etc. Aromatic polymers based on polyhydroxystyrene and its copolymers may also be used, especially for 248 nm exposure.

Polymers based on acrylates are generally based on poly (meth)acrylates with at least one unit containing pendant alicyclic groups, and with the acid labile group being pendant from the polymer backbone and/or from the alicyclic group. Examples of pendant alicyclic groups, may be adamantyl, tricyclodecyl, isobornyl, menthyl and their derivatives. Other pendant groups may also be incorporated into the polymer, such as mevalonic lactone, gamma butyrolactone, alkyloxyalkyl, etc. Examples of structures for the alicyclic group include:

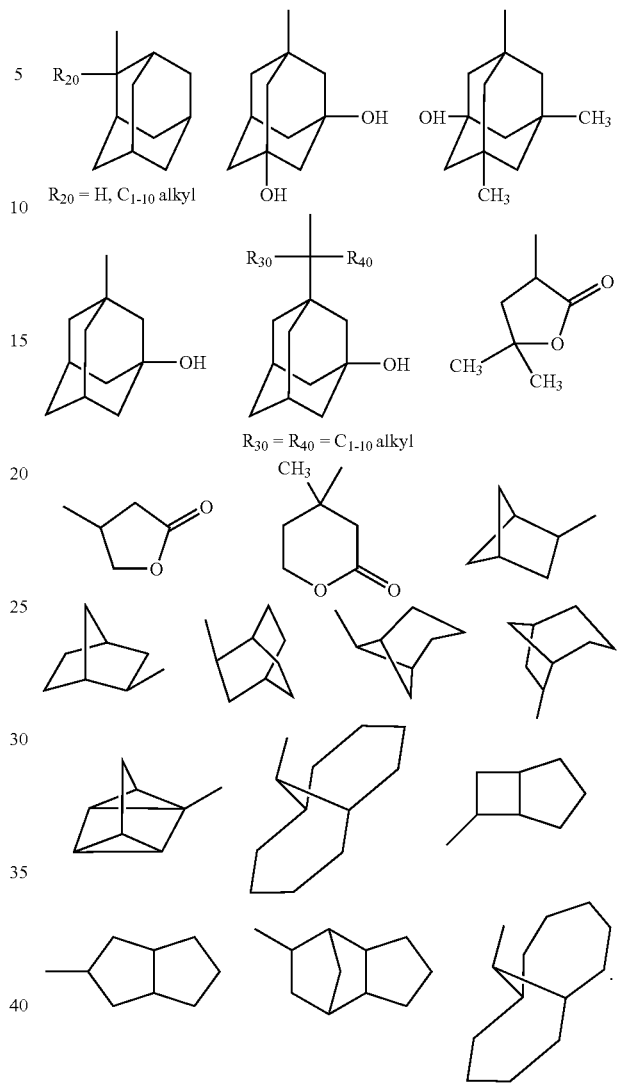

The type of monomers and their ratios incorporated into the polymer are optimized to give the best lithographic performance. Such polymers are described in R. R. Dammel et al., Advances in Resist Technology and Processing, SPIE, Vol. 3333, p 144, (1998). Examples of these polymers include poly(2-methyl-2-adamantyl methacrylate-co-mevalonic lactone methacrylate), poly(carboxy-tetracyclododecyl methacrylate-co-tetrahydropyranylcarboxytetracyclododecyl methacrylate), poly(tricyclodecylacrylate-co-tetrahydropyranylmethacrylate-co-methacrylicacid), poly(3-oxocyclohexyl methacrylate-co-adamantylmethacrylate).

Polymers synthesized from cycloolefins, with norbornene and tetracyclododecene derivatives, may be polymerized by ring-opening metathesis, free-radical polymerization or using metal organic catalysts. Cycloolefin derivatives may also be copolymerized with cyclic anhydrides or with maleimide or its derivatives. Examples of cyclic anhydrides are maleic anhydride (MA) and itaconic anhydride. The cycloolefin is incorporated into the backbone of the polymer and may be any substituted or unsubstituted multicyclic hydrocarbon containing an unsaturated bond. The monomer can have acid labile groups attached. The polymer may be synthesized from one or more cycloolefin monomers having an unsaturated bond. The cycloolefin monomers may be substituted or unsubstituted norbornene, or tetracyclododecane. The substituents on the cycloolefin may be aliphatic or cycloaliphatic alkyls, esters, acids, hydroxyl, nitrile or alkyl derivatives. Examples of cycloolefin monomers, without limitation, include:

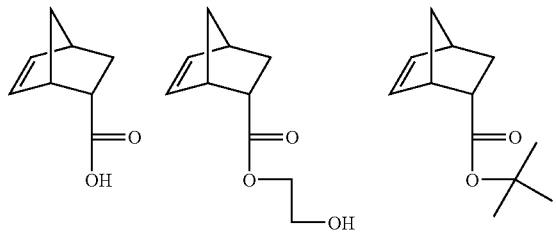

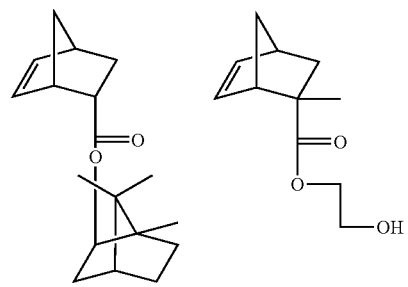

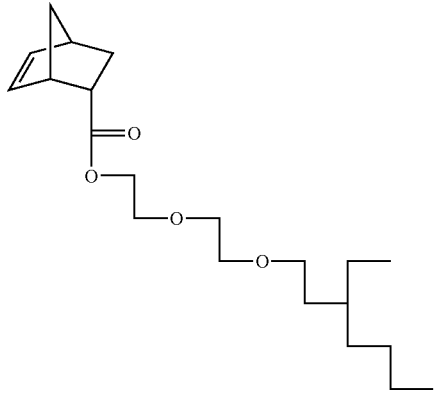

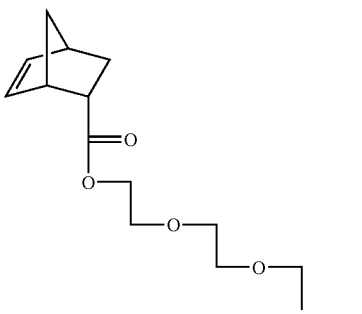

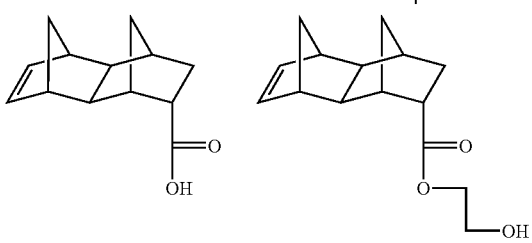

-continued

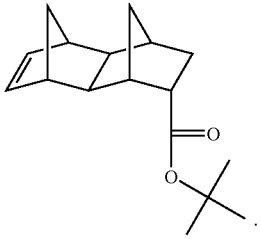

Other cycloolefin monomers which may also be used in synthesizing the polymer are:

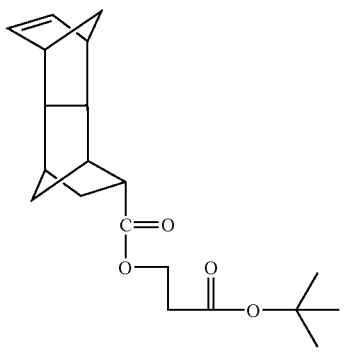

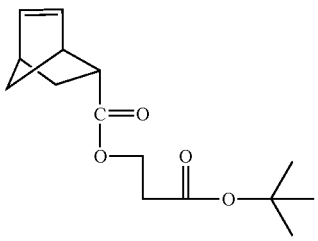

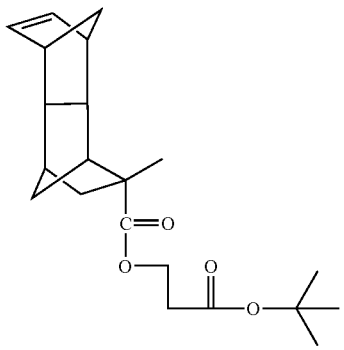

Such polymers are described in the following reference and incorporated herein, M-D. Rahman et al, Advances in Resist Technology and Processing, SPIE, Vol. 3678, p 1193, (1999). Examples of these polymers include poly((t-butyl-5-norbornene-2-carboxylate-co-2-hydroxyethyl-5-norbornene-2-carboxylate-co-5-norbornene-2-carboxylic acid-co-maleic anhydride), poly(t-butyl-5-norbornene-2-carboxylate-co-isobornyl-5-norbornene-2-carboxylate-co-2-hydroxyethyl-5-norbornene-2-carboxylate-co-5-norbornene-2-carboxylic acid-co-maleic an hydride), poly(tetracyclododecene-5-carboxylate-co-maleic an hydride), poly(t-butyl-5-norbornene-2-carboxylate-co-maleic anhydride-co-2-methyladamantyl methacrylate-co-2-mevalonic lactone methacrylate), poly(2-methyladamantyl methacrylate-co-2-mevalonic lactone methacylate) and the like.

Polymers containing mixtures of (meth)acrylate monomers, cycloolefinic monomers and cyclic anhydrides, where such monomers are described above, may also be combined into a hybrid polymer. Examples of cycloolefin monomers include those selected from t-butyl norbornene carboxylate (BNC), hydroxyethyl norbornene carboxylate (HNC), norbornene carboxylic acid (NC), t-butyltetracyclo[4.4.0.1.$^{2,}$ $^{6}$1.$^{7,10}$] dodec-8-ene-3-carboxylate, and t-butoxy carbonylmethyl tetracyclo[4.4.0.1.$^{2,6}$1.$^{7,10}$] dodec-8-ene-3-carboxylate. In some instances, preferred examples of cycloolefins include t-butyl norbornene carboxylate (BNC), hydroxyethyl norbornene carboxylate (HNC), and norbornene carboxylic acid (NC). Examples of (meth)acrylate monomers include those selected from mevalonic lactone methacrylate (MLMA), 2-methyl-2-adamantyl methacrylate (MAdMA), 2-adamantyl methacrylate (AdMA), 2-methyl-2-adamantyl acrylate (MAdA), 2-ethyl-2-adamantyl methacrylate (EAdMA), 3,5-dimethyl-7-hydroxy adamantyl methacrylate (DMHAdMA), adamantyl methyloxy methyl methacrylate (AdOMMA), isoadamantyl methacrylate, hydroxy-1-methacryloxyadamatane (HAdMA; for example, hydroxy at the 3-position), hydroxy-1-adamantyl acrylate (HADA; for example, hydroxy at the 3-position), ethylcyclopentylacrylate (ECPA), ethylcyclopentylmethacrylate (ECPMA), tricyclo[5,2,1,0$^{2,6}$] deca-8-yl methacrylate (TCDMA), 3,5-dihydroxy-1-methacryloxyadamantane (DHAdMA), β-methacryloxy-γ-butyrolactone, α- or β-gamma-butyrolactone methacrylate (either α- or β-GBLMA), 5-methacryloyloxy-2,6-norbornanecarbolactone (MNBL), 5-acryloyloxy-2,6-norbornanecarbolactone (ANBL), isobutyl methacrylate (IBMA), α-gamma-butyrolactone acrylate (α-GBLA), spirolactone (meth)acrylate, oxytricyclodecane (meth)acrylate, adamantane lactone (meth)acrylate, and α-methacryloxy-γ-butyrolactone, among others. Examples of polymers formed with these monomers include poly(2-methyl-2-adamantyl methacrylate-co-2-ethyl-2-adamantyl methacrylate-co-3-hydroxy-1-methacryloxyadamantane-co-α-gamma-butyrolactone methacrylate); poly(2-ethyl-2-adamantyl methacrylate-co-3-hydroxy-1-methacryloxyadamantane-co-β-gamma-butyrolactone methacrylate); poly(t-butyl norbornene carboxylate-co-maleic anhydride-co-2-methyl-2-adamantyl methacrylate-co-β-gamma-butyrolactone methacrylate-co-methacryloyloxy norbornene methacrylate); poly(2-methyl-2-adamantyl methacrylate-co-3-hydroxy-1-methacryloxyadamantane-co-β-gamma-butyrolactone methacrylate-co-tricyclo[5,2,1,0$^{2,6}$]deca-8-yl methacrylate); poly(2-ethyl-2-adamantyl methacrylate-co-3-hydroxy-1-adamantyl acrylate-co-β-gamma-butyrolactone methacrylate); poly(2-ethyl-2-adamantyl methacrylate-co-3-hydroxy-1-adamantyl acrylate-co-α-gamma-butyrolactone methacrylate-co-tricyclo[5,2,1,0$^{2,6}$]deca-8-yl methacrylate); poly(2-methyl-2-adamantyl methacrylate-co-3,5-dihydroxy-1-methacryloxyadamantane-co-α-gamma-butyrolactone methacrylate); poly(2-methyl-2-adamantyl methacrylate-co-3,5-dimethyl-7-hydroxy adamantyl methacrylate-co-α-gamma-butyrolactone methacrylate); poly(2-methyl-2-adamantyl acrylate-co-3-hydroxy-1-methacryloxyadamantane-co-α-gamma-butyrolactone methacrylate); poly(2-methyl-2-adamantyl methacrylate-co-3-hydroxy-1-methacryloxyadamantane-co-β-gamma-butyrolactone methacrylate-co-tricyclo[5,2,1,0$^{2,6}$]deca-8-yl methacrylate); poly(2-methyl-2-adamantyl methacrylate-co-β-gamma-butyrolactone methacrylate-co-3-hydroxy-1-methacryloxyadamantane-co-ethylcyclopentylacrylate); poly(2-methyl-2-adamantyl methacrylate-co-3-hydroxy-1-adamantyl acrylate-co-α-gamma-butyrolactone methacrylate); poly(2-methyl-2-adamantyl methacrylate-co-3-hydroxy-1-methacryloxyadamantane-co-α-gamma-butyrolactone methacrylate-co-2-ethyl-2-adamantyl methacrylate); poly(2-methyl-2-adamantyl methacrylate-co-3-hydroxy-1-methacryloxyadamantane-co-β-gamma-butyrolactone methacrylate-co-tricyclo[5,2,1,0$^{2,6}$] deca-8-yl methacrylate); poly(2-methyl-2-adamantyl methacrylate-co-2-ethyl-2-adamantyl methacrylate-co-β-gamma-butyrolactone methacrylate-co-3-hydroxy-1-methacryloxyadamantane); poly(2-methyl-2-adamantyl methacrylate-co-2-ethyl-2-adamantyl methacrylate-co-α-gamma-butyrolactone methacrylate-co-3-hydroxy-1-methacryloxyadamantane); poly(2-methyl-2-adamantyl methacrylate-co-methacryloyloxy norbornene methacrylate-co-β-gamma-butyrolactone methacrylate); poly(ethylcyclopentylmethacrylate-co-2-ethyl-2-adamantyl methacrylate-co-α-gamma-butyrolactone acrylate); poly(2-ethyl-2-adamantyl methacrylate-co-3-hydroxy-1-adamantyl acrylate-co-isobutyl methacrylate-co-α-gamma-butyrolactone acrylate); poly(2-methyl-2-adamantyl methacrylate-co-β-gamma-butyrolactone methacrylate-co-3-hydroxy-1-adamantyl acrylate-co-tricyclo[5,2,1,02,6]deca-8-yl methacrylate); poly(2-ethyl-2-adamantyl methacrylate-co-3-hydroxy-1-adamantyl acrylate-co-α-gamma-butyrolactone acrylate); poly(2-methyl-2-adamantyl methacrylate-co-β gamma-butyrolactone methacrylate-co-2-adamantyl methacrylate-co-3-hydroxy-1-methacryloxyadamatane); poly(2-methyl-2-adamantyl methacrylate-co-methacryloyloxy norbornene methacrylate-co-β-gamma-butyrolactone methacrylate-co-2-adamantyl methacrylate-co-3-hydroxy-1-methacryloxyadamatane); poly(2-methyl-2-adamantyl methacrylate-co-methacryloyloxy norbornene methacrylate-co-tricyclo[5,2,1,0$^{2,6}$]deca-8-yl methacrylate-co-3-hydroxy-1-methacryloxyadamatane-co-α-gamma-butyrolactone methacrylate); poly(2-ethyl-2-adamantyl methacrylate-co-3-hydroxy-1-adamantyl acrylate-co-tricyclo[5,2,1,0$^{2,6}$]deca-8-yl methacrylate-co-α-gamma-butyrolactone methacrylate); poly(2-ethyl-2-adamantyl methacrylate-co-3-hydroxy-1-adamantyl acrylate-co-α-gamma-butyrolactone acrylate); poly(2-methyl-2-adamantyl methacrylate-co-3-hydroxy-1-methacryloxyadamatane-co-α-gamma-butyrolactone methacrylate-co-2-ethyl-2-adamantyl-co-methacrylate); poly(2-ethyl-2-adamantyl methacrylate-co-3-hydroxy-1-adamantyl acrylate-co-α-gamma-butyrolactone methacrylate-co-tricyclo[5,2,1,0$^{2,6}$]deca-8-yl methacrylate); poly(2-ethyl-2-adamantyl methacrylate-co-3-hydroxy-1-adamantyl acrylate-co-α-gamma-butyrolactone methacrylate); poly(2-methyl-2-adamantyl methacrylate-co-3-hydroxy-1-adamantyl acrylate-co-5-acryloyloxy-2,6-norbornanecarbolactone); poly(2-ethyl-2-adamantyl methacrylate-co-3-hydroxy-1-adamantyl acrylate-co-α-gamma-butyrolactone methacrylate-co-α-gamma-butyrolactone acrylate); poly(2-ethyl-2-adamantyl methacrylate-co-3-hydroxy-1-adamantyl acrylate-co-α-gamma-butyrolactone methacrylate-co-2-adamantyl methacrylate); and poly(2-ethyl-2-adamantyl methacrylate-co-3-hydroxy-1-adamantyl acrylate-co-α-gamma-butyrolactone acrylate-co-tricyclo[5,2,1,02,6]deca-8-yl methacrylate).

Other examples of suitable polymers include those described in U.S. Pat. Nos. 6,610,465, 6,120,977, 6,136,504, 6,013,416, 5,985,522, 5,843,624, 5,693,453, 4,491,628, WO 00/25178, WO 00/67072, JP 2000-275845, JP 2000-137327, and JP 09-73173 which are incorporated herein by reference. Blends of one or more photoresist resins may be used. Standard synthetic methods are typically employed to make the various types of suitable polymers. Procedures or references to suitable standard procedures (e.g., free radical polymerization) can be found in the aforementioned documents.

The cycloolefin and the cyclic anhydride monomer are believed to form an alternating polymeric structure, and the amount of the (meth)acrylate monomer incorporated into the polymer can be varied to give the optimal lithographic properties. The percentage of the (meth)acrylate monomer relative to the cycloolefin/anhydride monomers within the polymer ranges from about 95 mole % to about 5 mole %, further ranging from about 75 mole % to about 25 mole %, and also further ranging from about 55 mole % to about 45 mole %.

Fluorinated non-phenolic polymers, useful for 157 nm exposure, also exhibit line edge roughness and can benefit from the use of the novel mixture of photoactive compounds described in the present invention. Such polymers are described in WO 00/17712 and WO 00/67072 and incorporated herein by reference. Example of one such polymer is poly(tetrafluoroethylene-co-norbornene-co-5-hexafluoroisopropanol-substituted 2-norbornene.

Polymers synthesized from cycloolefins and cyano containing ethylenic monomers are described in the U.S. Pat. No. 6,686,429, the contents of which are hereby incorporated herein by reference, may also be used.

The molecular weight of the polymers is optimized based on the type of chemistry used and on the lithographic performance desired. Typically, the weight average molecular weight is in the range of 3,000 to 30,000 and the polydispersity is in the range 1.1 to 5, preferably 1.5 to 2.5.

Other polymers of interest include those found and described in U.S. patent application Ser. No. 10/371,262, filed Feb. 21, 2003, now filed as U.S. patent application Ser. No. 10/658,840, filed Dec. 17, 2003 (and published now as US patent application publication no. 2004/0166433, the contents of which are incorporated herein by reference. Still other polymers, such as those disclosed in U.S. patent application Ser. No. 10/440,452, filed May 16, 2003 titled "Photoresist Composition for Deep UV and Process Thereof", the contents of which are hereby incorporated herein by reference, may also be used.

The solid components of the present invention are dissolved in an organic solvent. The amount of solids in the solvent or mixture of solvents ranges from about 1 weight % to about 50 weight %. The polymer may be in the range of 5 weight % to 90 weight % of the solids and the photoacid generator may be in the range of 1 weight % to about 50 weight % of the solids. Suitable solvents for such photoresists may include for example ketones such as acetone, methyl ethyl ketone, methyl isobutyl ketone, cyclohexanone, isophorone, methyl isoamyl ketone, 2-heptanone 4-hydroxy, and 4-methyl 2-pentanone; $C_1$ to $C_{10}$ aliphatic alcohols such as methanol, ethanol, and propanol; aromatic group containing-alcohols such as benzyl alcohol; cyclic carbonates such as ethylene carbonate and propylene carbonate; aliphatic or aromatic hydrocarbons (for example, hexane, toluene, xylene, etc and the like); cyclic ethers, such as dioxane and tetrahydrofuran; ethylene glycol; propylene glycol; hexylene glycol; ethylene glycol monoalkylethers such as ethylene glycol monomethylether, ethylene glycol monoethylether; ethylene glycol alkylether acetates such as methylcellosolve acetate and ethylcellosolve acetate; ethylene glycol dialkylethers such as ethylene glycol dimethylether, ethylene glycol diethylether, ethylene glycol methylethylether, diethylene glycol monoalkylethers such as diethylene glycol monomethylether, diethylene glycol monoethylether, and diethylene glycol dimethylether; propylene glycol monoalkylethers such as propylene glycol methylether, propylene glycol ethylether, propylene glycol propylether, and propylene glycol butylether; propylene glycol alkyletheracetates such as propylene glycol methylether acetate, propylene glycol ethylether acetate, propylene glycol propylether acetate, and propylene glycol butylether acetate; propylene glycol alkyletherpropionates such as propylene glycol methyletherpropionate, propylene glycol ethyletherpropionate, propylene glycol propyletherpropionate, and propylene glycol butyletherpropionate; 2-methoxyethyl ether (diglyme); solvents that have both ether and hydroxy moieties such as methoxy butanol, ethoxy butanol, methoxy propanol, and ethoxy propanol; esters such as methyl acetate, ethyl acetate, propyl acetate, and butyl acetate methyl-pyruvate, ethyl pyruvate; ethyl 2-hydroxy propionate, methyl 2-hydroxy 2-methyl propionate, ethyl 2-hydroxy 2-methyl propionate, methyl hydroxy acetate, ethyl hydroxy acetate, butyl hydroxy acetate, methyl lactate, ethyl lactate, propyl lactate, butyl lactate, methyl 3-hydroxy propionate, ethyl 3-hydroxy propionate, propyl 3-hydroxy propionate, butyl 3-hydroxy propionate, methyl 2-hydroxy 3-methyl butanoic acid, methyl methoxy acetate, ethyl methoxy acetate, propyl methoxy acetate, butyl methoxy acetate, methyl ethoxy acetate, ethyl ethoxy acetate, propyl ethoxy acetate, butyl ethoxy acetate, methyl propoxy acetate, ethyl propoxy acetate, propyl propoxy acetate, butyl propoxy acetate, methyl butoxy acetate, ethyl butoxy acetate, propyl butoxy acetate, butyl butoxy acetate, methyl 2-methoxy propionate, ethyl 2-methoxy propionate, propyl 2-methoxy propionate, butyl 2-methoxy propionate, methyl 2-ethoxypropionate, ethyl 2-ethoxypropionate, propyl 2-ethoxypropionate, butyl 2-ethoxypropionate, methyl 2-butoxypropionate, ethyl 2-butoxypropionate, propyl 2-butoxypropionate, butyl 2-butoxypropionate, methyl 3-methoxypropionate, ethyl 3-methoxypropionate, propyl 3-methoxypropionate, butyl 3-methoxypropionate, methyl 3-ethoxypropionate, ethyl 3-ethoxypropionate, propyl 3-ethoxypropionate, butyl 3-ethoxypropionate, methyl 3-propoxypropionate, ethyl 3-propoxypropionate, propyl 3-propoxypropionate, butyl 3-propoxypropionate, methyl 3-butoxypropionate, ethyl 3-butoxypropionate, propyl 3-butoxypropionate, and butyl 3-butoxypropionate; oxyisobutyric acid esters, for example, methyl-2-hydroxyisobutyrate, methyl α-methoxyisobutyrate, ethyl methoxyisobutyrate, methyl α-ethoxyisobutyrate, ethyl α-ethoxyisobutyrate, methyl β-methoxyisobutyrate, ethyl β-methoxyisobutyrate, methyl β-ethoxyisobutyrate, ethyl β-ethoxyisobutyrate, methyl β-isopropoxyisobutyrate, ethyl β-isopropoxyisobutyrate, isopropyl β-isopropoxyisobutyrate, butyl β-isopropoxyisobutyrate, methyl β-butoxyisobutyrate, ethyl β-butoxyisobutyrate, butyl β-butoxyisobutyrate, methyl α-hydroxyisobutyrate, ethyl α-hydroxyisobutyrate, isopropyl α-hydroxyisobutyrate, and butyl α-hydroxyisobutyrate; solvents that have both ether and hydroxy moieties such as methoxy butanol, ethoxy butanol, methoxy propanol, and ethoxy propanol; and other solvents such as dibasic esters, and gamma-butyrolactone; a ketone ether derivative such as diacetone alcohol methyl ether; a ketone alcohol derivative such as acetol or diacetone alcohol; lactones such as butyrolactone; an amide derivative such as dimethylacetamide or dimethylformamide, anisole, and mixtures thereof.

Various other additives such as colorants, non-actinic dyes, anti-striation agents, plasticizers, adhesion promoters, dissolution inhibitors, coating aids, photospeed enhancers, additional photoacid generators, and solubility enhancers (for example, certain small levels of solvents not used as part of the main solvent (examples of which include glycol ethers and glycol ether acetates, valerolactone, ketones, lactones, and the like), and surfactants may be added to the photoresist composition before the solution is coated onto a substrate. Surfactants that improve film thickness uniformity, such as fluorinated surfactants, can be added to the photoresist solution. A sensitizer that transfers energy from a particular range of wavelengths to a different exposure wavelength may also be added to the photoresist composition. Often bases are also added to the photoresist to prevent t-tops or bridging at the surface of the photoresist image. Examples of bases are amines, ammonium hydroxide, and photosensitive bases. Particularly preferred bases are trioctylamine, diethanolamine and tetrabutylammonium hydroxide.

The prepared photoresist composition solution can be applied to a substrate by any conventional method used in the photoresist art, including dipping, spraying, and spin coating. When spin coating, for example, the photoresist solution can be adjusted with respect to the percentage of solids content, in order to provide coating of the desired thickness, given the type of spinning equipment utilized and the amount of time allowed for the spinning process. Suitable substrates include silicon, aluminum, polymeric resins, silicon dioxide, doped silicon dioxide, silicon nitride, tantalum, copper, polysilicon, ceramics, aluminum/copper mixtures; gallium arsenide and other such Group III/V compounds. The photoresist may also be coated over antireflective coatings.

The photoresist coatings produced by the described procedure are particularly suitable for application to silicon/silicon dioxide wafers, such as are utilized in the production of microprocessors and other miniaturized integrated circuit components. An aluminum/aluminum oxide wafer can also be used. The substrate may also comprise various polymeric resins, especially transparent polymers such as polyesters.

The photoresist composition solution is then coated onto the substrate, and the substrate is treated (baked) at a temperature from about 70° C. to about 150° C. for from about 30 seconds to about 180 seconds on a hot plate or for from about 15 to about 90 minutes in a convection oven. This temperature treatment is selected in order to reduce the concentration of residual solvents in the photoresist, while not causing substantial thermal degradation of the solid components. In general, one desires to minimize the concentration of solvents and this first temperature. Treatment (baking) is conducted until substantially all of the solvents have evaporated and a thin coating of photoresist composition, on the order of half a micron (micrometer) in thickness, remains on the substrate. In a preferred embodiment the temperature is from about 95° C. to about 120° C. The treatment is conducted until the rate of change of solvent removal becomes relatively insignificant. The film thickness, temperature and time selection depends on the photoresist properties desired by the user, as well as the equipment used and commercially desired coating times. The coated substrate can then be imagewise exposed to actinic radiation, e.g., ultraviolet radiation, at a wavelength of from about 100 nm (nanometers) to about 300 nm, x-ray, electron beam, ion beam or laser radiation, in any desired pattern, produced by use of suitable masks, negatives, stencils, templates, etc.

The photoresist is then subjected to a post exposure second baking or heat treatment before development. The heating temperatures may range from about 90° C. to about 150° C., more preferably from about 100° C. to about 130° C. The heating may be conducted for from about 30 seconds to about 2 minutes, more preferably from about 60 seconds to about 90 seconds on a hot plate or about 30 to about 45 minutes by convection oven.

The exposed photoresist-coated substrates are developed to remove the image-wise exposed areas by immersion in a developing solution or developed by spray development process. The solution is preferably agitated, for example, by nitrogen burst agitation. The substrates are allowed to remain in the developer until all, or substantially all, of the photoresist coating has dissolved from the exposed areas. Developers include aqueous solutions of ammonium or alkali metal hydroxides. One preferred developer is an aqueous solution of tetramethyl ammonium hydroxide. After removal of the coated wafers from the developing solution, one may conduct an optional post-development heat treatment or bake to increase the coating's adhesion and chemical resistance to etching conditions and other substances. The post-development heat treatment can comprise the oven baking of the coating and substrate below the coating's softening point or UV hardening process. In industrial applications, particularly in the manufacture of microcircuitry units on silicon/silicon dioxide-type substrates, the developed substrates may be treated with a buffered, hydrofluoric acid base etching solution or dry etching. Prior to dry etching the photoresist may be treated to electron beam curing in order to increase the dry-etch resistance of the photoresist.

The invention further provides a method for producing a semiconductor device by producing a photo-image on a substrate by coating a suitable substrate with a photoresist composition. The subject process comprises coating a suitable substrate with a photoresist composition and heat treating the coated substrate until substantially all of the photoresist solvent is removed; image-wise exposing the composition and removing the image-wise exposed areas of such composition with a suitable developer.

The following examples provide illustrations of the methods of producing and utilizing the present invention. These examples are not intended, however, to limit or restrict the scope of the invention in any way and should not be construed as providing conditions, parameters or values which must be utilized exclusively in order to practice the present invention. Unless otherwise specified, all parts and percents are by weight.

EXAMPLE 1

Synthesis of bis[di(4-t-butyl phenyl) iodonium] di-(tetrafluoroethyl sulfonate) ether

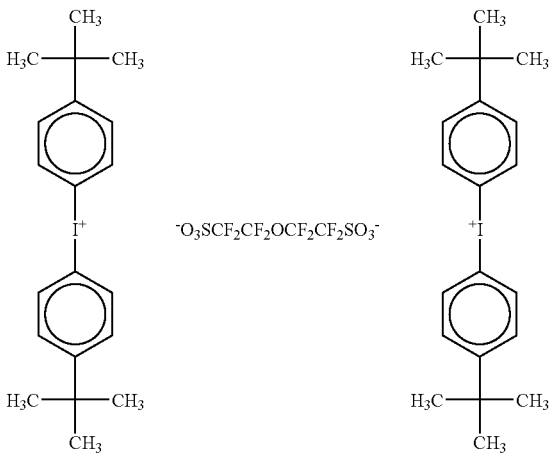

Bis[2-(fluorosulfonyl)tetrafluoroethyl]ether obtained from Synquest (5 g) was taken in a flask in water and excess amount of KOH was and heated under stirring at 80° C. for six hours. The solution was cooled to room temperature and di t-butylphenylphenyl iodonium acetate (2 mol equivalent) in water and THF was added on stirring. After six hours, chloroform was added and stirred for 3 hours. The chloroform layer was washed several times with water, dried over anhydrous sodium sulfate, filtered and chloroform evaporated. Hexane was added to form crystals, filtered and dried under vacuum, mp 101° C. 6.5 g was isolated.

EXAMPLE 2

Synthesis of bis[(triphenyl) sulfonium] di-(tetrafluoroethyl sulfonate) ether

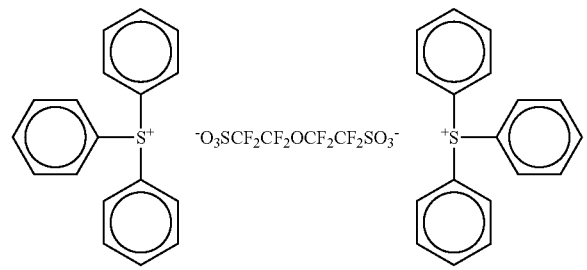

Bis[2-(fluorosulfonyl)tetrafluoroethyl]ether obtained from Synquest (5 g) was taken in a flask in water and excess amount of KOH (2.93 g) was and heated under stirring at 80° C. for six hours. The solution was cooled to room temperature and triphenyl sulfonium bromide (2 mole equivalent) in water and THF was added on stirring. After 3 hours, dichloromethane was added and stirred for 2 hours. The dichloromethane layer was washed several times with water, dried over anhydrous sodium sulfate, filtered and dichloromethane evaporated. Hexane was added to form crystals, filtered and dried under vacuum, mp 86-87° C. 8.0 g was isolated.

EXAMPLE 3

Synthesis of bis[(4-octyloxyphenyl phenyl) iodonium] di-(tetrafluoroethyl sulfonate) ether

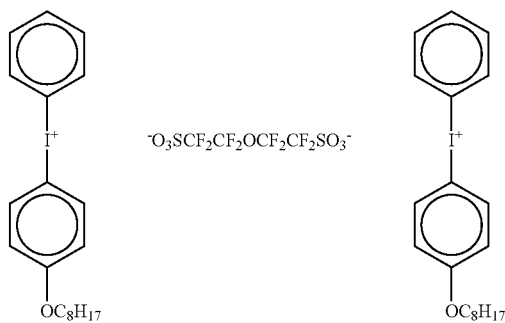

Bis[2-(fluorosulfonyl)tetrafluoroethyl]ether obtained from Synquest (5 g) was taken in a flask in water and excess amount of KOH (2.9 g) was and heated under stirring at 80° C. for six hours. The solution was cooled to room temperature and 4-octyloxyphenyl phenyl iodonium chloride (11.64 g) in water and THF was added on stirring. After six hours, chloroform was added and stirred for 3 hours. The chloroform layer was washed several times with water, dried over anhydrous sodium sulfate, filtered and chloroform evaporated. Hexane was added on stirring, separated as oil layer, decanted and dried under vacuum. (14.5 g) was isolated as oil.

EXAMPLE 4

Synthesis of bis[(diphenyl) iodonium] di-(tetrafluoroethyl sulfonate) ether

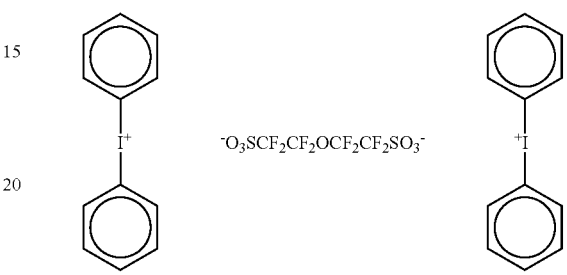

Bis[2-(fluorosulfonyl)tetrafluoroethyl]ether obtained from Synquest (5 g) was taken in a flask in water and excess amount of KOH (2.9 g) was and heated under stirring at 80° C. for six hours. The solution was cooled to room temperature and di phenyl iodonium chloride 8.2 g) in water and THF was added on stirring. After six hours, chloroform was added and stirred for 3 hours. The chloroform layer was washed several times with water, dried over anhydrous sodium sulfate, filtered and chloroform evaporated. Hexane was added on stirring and white crystals were formed. The solution was filtered and the white crystals were washed with hexane. The crystals were dried under vacuum and isolated (6.5 g; mp 210° C.).

Following the procedure in Example 1, the following compounds can be made from the corresponding iodonium acetate or halide or sulfonium acetate or halide: bis[di(4-octyloxyphenyl) iodonium] di-(tetrafluoroethyl sulfonate) ether bis[(4-methylphenyl)phenyl iodonium] di-(tetrafluoroethyl sulfonate) ether bis[(4-t-butylphenyl)phenyl iodonium] di-(tetrafluoroethyl sulfonate) ether bis[(4-methoxyphenyl) phenyl iodonium] di-(tetrafluoroethyl sulfonate) ether bis(4-methoxyphenyl) iodonium di-(tetrafluoroethyl sulfonate) ether bis(4-t-butylphenyl diphenyl sulfonium) di-(tetrafluoroethyl sulfonate) ether bis(4-t-butylphenyl iodonium) di-(tetrafluoroethyl sulfonate) ether bis(4-t-butylphenyl iodonium) triphenyl sulfonium di-(tetrafluoroethyl sulfonate) ether bis(benzoyltetramethylenesulfonium) di-(tetrafluoroethyl sulfonate) ether bis(triphenyl sulfonium) di-(tetrafluoroethyl sulfonate) ether bis(tris(4-t-butyl phenyl) sulfonium) di-(tetrafluoroethyl sulfonate) ether bis[bis[2-methyl-adamantylacetyloxymethoxyphenyl]phenylsulfonium] di-(tetrafluoroethyl sulfonate) ether bis[bis[4-(3,5-di(trifluoromethyl)benzenesulfonyloxy)-phenyl]phenylsulfonium] di-(tetrafluoroethyl sulfonate) ether bis[bis[4,4-bis(trifluoromethyl)-3-oxatricyclo[4.2.1.0$^{2,5}$]-nonylmethoxyphenyl] phenyl sulfonium] di-(tetrafluoroethyl sulfonate) ether bis [bis[4-pentafluorobenzenesulfonyloxyphenyl] phenylsulfonium] di-(tetrafluoroethyl sulfonate) ether

EXAMPLE 5

0.5352 g of poly(EAdMA/AdOMMA/HAdA/α-GBLMA/ AdMA; 20/10/20/40/10) polymer, 0.0124 g (30 μmol/g) of bis(4-t-butylphenyl) iodonium bis-perfluoroethane sulfonimide and 0.0142 g (30 μmol/g) of bis(triphenyl sulfonium) perfluorobutane-1,4-disulfonate, and 0.0292 g (47 μmol/g) of bis[di(4-t-butyl phenyl) iodonium] di-(tetrafluoroethyl sulfonate) ether from Example 1, 0.3919 g of DIPA 1 weight % in PGMEA) and 0.0204 g of 10 weight % PGMEA solution of a surfactant (fluoroaliphatic polymeric ester, supplied by 3M Corporation, St. Paul Minn.) were dissolved in 13.122 g of MHIB and 3.224 g of PGME to give a 17 g photoresist solution.

EXAMPLE 6

A silicon substrate coated with a bottom antireflective coating (B.A.R.C.) was prepared by spin coating the bottom antireflective coating solution (AZ® ArF-38, available from AZ Electronic Materials Corporation, Somerville, N.J.) onto the silicon substrate and baked at 225° C. for 90 sec. The B.A.R.C film thickness was 87 nm. The photoresist solution from Example 5 was then coated on the B.A.R.C coated silicon substrate. The spin speed was adjusted such that the photoresist film thickness was 300 nm, soft baked at 10° C./60 s, exposed with Nikon 306D 0.78 NA & 4/5 Annular Illumination using a binary mask; then the wafer was post exposure baked at 110° C./60 s, and developed using a 2.38 weight % aqueous solution of tetramethyl ammonium hydroxide for 30 sec. The line and space patterns were then observed on a scanning electron microscope. The photoresist had a photosensitivity of 68.0 mJ/cm$^2$ and had very good exposure latitude (18.7%), good LER and profile shape.

EXAMPLE 7

0.6443 g of poly(EAdMA/HAdA/α-GBLMA/AdMA; 30/20/40/10) polymer, 0.0199 g (40 μmol/g) of bis(4-t-butylphenyl) iodonium bis-perfluoroethane sulfonimide and 0.0171 g (30 μmol/g) of bis(triphenyl sulfonium) perfluorobutane-1,4-disulfonate, and 0.0150 g (20 μmol/g) of bis[di(4-t-butyl phenyl) iodonium] di-(tetrafluoroethyl sulfonate) ether from Example 1, 0.3598 g of DIPA 1 weight % in PGMEA) and 0.0204 g of 10 weight % PGMEA solution of a surfactant (fluoroaliphatic polymeric ester, supplied by 3M Corporation, St. Paul Minn.) were dissolved in 13.122 g of MHIB and 3.7914 g of PGME to give a 20 g photoresist solution.

EXAMPLE 8

A silicon substrate coated with a bottom antireflective coating (B.A.R.C.) was prepared by spin coating the bottom antireflective coating solution (AZ® ArF-38, available from AZ Electronic Materials Corporation, Somerville, N.J.) onto the silicon substrate and baking at 225° C. for 90 sec. The B.A.R.C film thickness was 87 nm. The photoresist solution from Example 7 was then coated on the B.A.R.C coated silicon substrate. The spin speed was adjusted such that the photoresist film thickness was 300 nm, soft baked at 100° C./60 s, exposed with Nikon 306D 0.78 NA & 4/5 Annular Illumination using a binary mask; then the wafer was post exposure baked at 110° C./60 s, and developed using a 2.38 weight % aqueous solution of tetramethyl ammonium hydroxide for 30 sec. The line and space patterns were then observed on a scanning electron microscope. The photoresist had a photosensitivity of 68.0 mJ/cm$^2$ and had very good exposure latitude (18.7%), good LER and profile shape.

EXAMPLE 9

0.5352 g of poly(ECPMA/HAdA/α-GBLMA; 30/30/40) polymer, 0.0124 g (30 μmol/g) of bis(4-t-butylphenyl) iodonium bis-perfluoroethane sulfonimide and 0.0142 g (30 μmol/g) of bis(triphenyl sulfonium) perfluorobutane-1,4-disulfonate, and 0.0292 g (47 μmol/g) of bis[di(4-t-butyl phenyl) iodonium] di-(tetrafluoroethyl sulfonate) ether from Example 1, 0.3919 g of DIPA 1 weight % in PGMEA) and 0.0204 g of 10 weight % PGMEA solution of a surfactant (fluoroaliphatic polymeric ester, supplied by 3M Corporation, St. Paul Minn.) were dissolved in 13.122 g of MHIB and 3.224 g of PGME to give a 17 g photoresist solution.

EXAMPLE 10

A silicon substrate coated with a bottom antireflective coating (B.A.R.C.) was prepared by spin coating the bottom antireflective coating solution (AZ® ArF-38, available from AZ Electronic Materials Corporation, Somerville, N.J.) onto the silicon substrate and baking at 225° C. for 90 sec. The B.A.R.C film thickness was 87 nm. The photoresist solution from Example 9 was then coated on the B.A.R.C coated silicon substrate. The spin speed was adjusted such that the photoresist film thickness was thickness 300 nm, soft baked at 100° C./60 s, exposed with Nikon 306D 0.78 NA & 4/5 Annular Illumination using a binary mask; then the wafer was post exposure baked at 110° C./60 s, and developed using a 2.38 weight % aqueous solution of tetramethyl ammonium hydroxide for 30 sec. The line and space patterns were then observed on a scanning electron microscope. The photoresist had a photosensitivity of 68.0 mJ/cm$^2$ and had very good exposure latitude (18.7%), good LER and profile shape.

EXAMPLE 11

0.5352 g of poly(EAdMA/ECPMA/HAdA/α-GBLMA; 15/15/30/40) polymer, 0.0124 g (30 μmol/g) of bis(4-t-butylphenyl) iodonium bis-perfluoroethane sulfonimide and 0.0142 g (30 μmol/g) of bis(triphenyl sulfonium) perfluorobutane-1,4-disulfonate, and 0.0292 g (47 μmol/g) of bis[di(4-t-butyl phenyl) iodonium] di-(tetrafluoroethyl sulfonate) ether from Example 1, 0.3919 g of DIPA 1 weight % in PGMEA) and 0.0204 g of 10 weight % PGMEA solution of a surfactant (fluoroaliphatic polymeric ester, supplied by 3M Corporation, St. Paul Minn.) were dissolved in 13.122 g of MHIB and 3.224 g of PGME to give a 17 g photoresist solution.

EXAMPLE 12

A silicon substrate coated with a bottom antireflective coating (B.A.R.C.) was prepared by spin coating the bottom antireflective coating solution (AZ® ArF-38, available from AZ Electronic Materials Corporation, Somerville, N.J.) onto the silicon substrate and baking at 225° C. for 90 sec. The B.A.R.C film thickness was 87 nm. The photoresist solution from Example 11 was then coated on the B.A.R.C coated silicon substrate. The spin speed was adjusted such that the photoresist film thickness was 300 nm, soft baked at 100° C./60 s, exposed with Nikon 306D 0.78 NA & 4/5 Annular Illumination using a binary mask; then the wafer was post exposure baked at 110° C./60 s, and developed using a 2.38 weight % aqueous solution of tetramethyl ammonium hydroxide for 30 sec. The line and space patterns were then observed on a scanning electron microscope. The photoresist had a photosensitivity of 68.0 mJ/cm$^2$ and had very good exposure latitude (18.7%), good LER and profile shape.

EXAMPLE 13

0.6291 g of poly(EAdMA/ECPMA/AdOMMA/HAdA/α-GBLMA; 5/15/10/30/40) polymer, 0.0146 g (30 μmol/g) of bis(4-t-butylphenyl) iodonium bis-perfluoroethane sulfonimide and 0.0142 g (30 μmol/g) of bis(triphenyl sulfonium) perfluorobutane-1,4-disulfonate, and 0.0170 g (47 μmol/g) of bis[di(triphenyl) sulfonium] di-(tetrafluoroethyl sulfonate) ether from Example 2, 0.5336 g of DIPA 1 weight % Q9 (DBA in MHIB) and 0.0204 g of 10 weight % PGMEA solution of a surfactant (fluoroaliphatic polymeric ester, supplied by 3M Corporation, St. Paul Minn.) were dissolved in 11.3994 g of MHIB and 3.7918 g of PGME to give a 20 g photoresist solution.

EXAMPLE 14

A silicon substrate coated with a bottom antireflective coating (B.A.R.C.) was prepared by spin coating the bottom anti-reflective coating solution (AZ® ArF-38, available from AZ Electronic Materials Corporation, Somerville, N.J.) onto the silicon substrate and baking at 225° C. for 90 sec. The B.A.R.C film thickness was 87 nm. The photoresist solution from Example 13 was then coated on the B.A.R.C coated silicon substrate. The spin speed was adjusted such that the photoresist film thickness was 300 nm, soft baked at 100° C./60 s, exposed with Nikon 306D 0.78 NA & 4/5 Annular Illumination using a binary mask; then the wafer was post exposure baked at 110° C./60 s, and developed using a 2.38 weight % aqueous solution of tetramethyl ammonium hydroxide for 30 sec. The line and space patterns were then observed on a scanning electron microscope. The photoresist had a photosensitivity of 37.5 mJ/cm$^2$ and had very good exposure latitude (8.52%), good LER and profile shape.

EXAMPLE 15

Examples 5, 7, 9, 11, and 13 can be repeated by substituting the polymer therein with one of the following polymers: poly(2-methyl-2-adamantyl methacrylate-co-2-ethyl-2-adamantyl methacrylate-co-3-hydroxy-1-methacryloxyadamantane-co-α-gamma-butyrolactone methacrylate); poly(2-ethyl-2-adamantyl methacrylate-co-3-hydroxy-1-methacryloxyadamantane-co-β-gamma-butyrolactone methacrylate); poly(2-methyl-2-adamantyl methacrylate-co-3-hydroxy-1-methacryloxyadamantane-co-β-gamma-butyrolactone methacrylate); poly(t-butyl norbornene carboxylate-co-maleic anhydride-co-2-methyl-2-adamantyl methacrylate-co-β-gamma-butyrolactone methacrylate-co-methacryloyloxy norbornene methacrylate); poly(2-methyl-2-adamantyl methacrylate-co-3-hydroxy-1-methacryloxyadamantane-co-β-gamma-butyrolactone methacrylate-co-tricyclo[5,2,1,0$^{2,6}$]deca-8-yl methacrylate); poly(2-ethyl-2-adamantyl methacrylate-co-3-hydroxy-1-adamantyl acrylate-co-β-gamma-butyrolactone methacrylate); poly(2-ethyl-2-adamantyl methacrylate-co-3-hydroxy-1-adamantyl acrylate-co-α-gamma-butyrolactone methacrylate-co-tricyclo[5,2,1,0$^{2,6}$]deca-8-yl methacrylate); poly(2-methyl-2-adamantyl methacrylate-co-3,5-dihydroxy-1-methacryloxyadamantane-co-α-gamma-butyrolactone methacrylate); poly(2-methyl-2-adamantyl methacrylate-co-3,5-dimethyl-7-hydroxy adamantyl methacrylate-co-α-gamma-butyrolactone methacrylate); poly(2-methyl-2-adamantyl acrylate-co-3-hydroxy-1-methacryloxyadamantane-co-α-gamma-butyrolactone methacrylate); poly(2-methyl-2-adamantyl methacrylate-co-3-hydroxy-1-methacryloxyadamantane-co-β-gamma-butyrolactone methacrylate-co-tricyclo[5,2,1,0$^{2,6}$]deca-8-yl methacrylate); poly(2-methyl-2-adamantyl methacrylate-co-β-gamma-butyrolactone methacrylate-co-ethylcyclopentylacrylate); poly(2-methyl-2-adamantyl methacrylate-co-3-hydroxy-1-adamantyl acrylate-co-α-gamma-butyrolactone methacrylate); poly(2-methyl-2-adamantyl methacrylate-co-3-hydroxy-1-methacryloxyadamantane-co-α-gamma-butyrolactone methacrylate-co-2-ethyl-2-adamantyl methacrylate); poly(2-methyl-2-adamantyl methacrylate-co-3-hydroxy-1-methacryloxyadamantane-co-β-gamma-butyrolactone methacrylate-co-tricyclo[5,2,1,0$^{2,6}$] deca-8-yl methacrylate); poly(2-methyl-2-adamantyl methacrylate-co-2-ethyl-2-adamantyl methacrylate-co-β-gamma-butyrolactone methacrylate-co-3-hydroxy-1-methacryloxyadamantane); poly(2-methyl-2-adamantyl methacrylate-co-2-ethyl-2-adamantyl methacrylate-co-α-gamma-butyrolactone methacrylate-co-3-hydroxy-1-methacryloxyadamantane); poly(2-methyl-2-adamantyl methacrylate-co-methacryloyloxy norbornene methacrylate-co-β-gamma-butyrolactone methacrylate); poly (ethylcyclopentylmethacrylate-co-2-ethyl-2-adamantyl methacrylate-co-α-gamma-butyrolactone acrylate); poly(2-ethyl-2-adamantyl methacrylate-co-3-hydroxy-1-adamantyl acrylate-co-isobutyl methacrylate-co-α-gamma-butyrolactone acrylate); poly(2-methyl-2-adamantyl methacrylate-co-β-gamma-butyrolactone methacrylate-co-3-hydroxy-1-adamantyl acrylate-co-tricyclo[5,2,1,02,6]deca-8-yl methacrylate); poly(2-ethyl-2-adamantyl methacrylate-co-3-hydroxy-1-adamantyl acrylate-co-α-gamma-butyrolactone acrylate); poly(2-methyl-2-adamantyl methacrylate-co-β gamma-butyrolactone methacrylate-co-2-adamantyl methacrylate-co-3-hydroxy-1-methacryloxyadamatane); poly(2-methyl-2-adamantyl methacrylate-co-methacryloyloxy norbornene methacrylate-co-β-gamma-butyrolactone methacrylate-co-2-adamantyl methacrylate-co-3-hydroxy-1-methacryloxyadamatane); poly(2-methyl-2-adamantyl methacrylate-co-methacryloyloxy norbornene methacrylate-co-tricyclo[5,2,1,02,6]deca-8-yl methacrylate-co-3-hydroxy-1-methacryloxyadamatane-co-α-gamma-butyrolactone methacrylate); poly(2-ethyl-2-adamantyl methacrylate-co-3-hydroxy-1-adamantyl acrylate-co-tricyclo[5,2,1,02,6] deca-8-yl methacrylate-co-α-gamma-butyrolactone methacrylate); poly(2-ethyl-2-adamantyl methacrylate-co-3-hydroxy-1-adamantyl acrylate-co-α-gamma-butyrolactone acrylate); poly(2-methyl-2-adamantyl methacrylate-co-3-hydroxy-1-methacryloxyadamatane-co-α-gamma-butyrolactone methacrylate-co-2-ethyl-2-adamantyl-co-methacrylate); poly(2-ethyl-2-adamantyl methacrylate-co-3-hydroxy-1-adamantyl acrylate-co-α-gamma-butyrolactone methacrylate-co-tricyclo[5,2,1,0$^{2,6}$]deca-8-yl methacrylate); poly(2-ethyl-2-adamantyl methacrylate-co-3-hydroxy-1-adamantyl acrylate-co-α-gamma-butyrolactone methacrylate-co-2-adamantyl methacrylate); poly(2-ethyl-2-adamantyl methacrylate-co-3-hydroxy-1-adamantyl acrylate-co-α-gamma-butyrolactone methacrylate); and poly(2-ethyl-2-adamantyl methacrylate-co-3-hydroxy-1-adamantyl acrylate-co-α-gamma-butyrolactone acrylate-co-tricyclo[5,2,1,02,6]deca-8-yl methacrylate) to form a photoresist solution. The photoresist solutions formed therefrom are expected to give similar results as to those found in Examples 4, 6, 8, and 10.

EXAMPLE 16

Example 15 can be repeated by replacing bis[di(4-t-butyl phenyl) iodonium] di-(tetrafluoroethyl sulfonate) ether from Example 1 with one of the following: bis [di(4-octyloxyphenyl) iodonium] di-(tetrafluoroethyl sulfonate) ether, bis[(4-octyloxyphenyl)phenyl iodonium] di-(tetrafluoroethyl sulfonate) ether, bis[(4-methylphenyl)phenyl iodonium] di-(tetrafluoroethyl sulfonate) ether, bis[(4-t-butylphenyl) phenyl iodonium] di-(tetrafluoroethyl sulfonate) ether, bis [(4-methoxyphenyl)phenyl iodonium] di-(tetrafluoroethyl sulfonate) ether, bis(4-methoxyphenyl) iodonium di-(tetrafluoroethyl sulfonate) ether, bis(4-octyloxyphenyl)phenyl sulfonium di-(tetrafluoroethyl sulfonate) ether, bis(4-t-butylphenyl diphenyl sulfonium) di-(tetrafluoroethyl sulfonate) ether, bis(4-t-butylphenyl iodonium) di-(tetrafluoroethyl sulfonate) ether, bis(4-t-butylphenyl iodonium) triphenyl sulfonium di-(tetrafluoroethyl sulfonate) ether, bis(benzoyltetramethylenesulfonium) di-(tetrafluoroethyl sulfonate) ether, bis(tris(4-t-butyl phenyl) sulfonium) di-(tetrafluoroethyl sulfonate) ether, bis[bis[2-methyl-adamantylacetyloxymethoxyphenyl]phenylsulfonium] di-(tetrafluoroethyl sulfonate) ether, bis[bis[4-(3,5-di(trifluoromethyl)benzenesulfonyloxy)-phenyl]phenylsulfonium] di-(tetrafluoroethyl sulfonate) ether, bis[bis[4,4-bis(trifluoro-methyl)-3-oxatricyclo [4.2.1.0$^{2,5}$]-nonylmethoxyphenyl]phenyl sulfonium] di-(tetrafluoroethyl sulfonate) ether, or bis[bis[4-pentafluorobenzenesulfonyloxyphenyl]phenylsulfonium] di-(tetrafluoroethyl sulfonate) ether. The photoresist solutions formed therefrom are expected to give similar results as to those found in Examples 6, 8, 10, 12, and 14.

The additional photoacid generators of formula Ai Xi1 Bi can be made in accordance with the procedures set forth in U.S. patent application Ser. Nos. 11/179,886, filed Jul. 12, 2005, and 11/355,762, filed Feb. 16, 2006, the contents of which are hereby incorporated herein by reference. Other examples are found in U.S. patent application Ser. No. 11/355,400, filed Feb. 16, 2006, United States Published Patent Application 2004-0229155, and United States Published Patent Application 2005-0271974, U.S. Pat. No. 5,837,420, U.S. Pat. No. 6,111,143, and U.S. Pat. No. 6,358,665, the contents of which are hereby incorporated herein by reference. Those additional photoacid generators of formula Ai Xi2 are well known to those skilled in the art, for example, those known from United States Patent Application No. 20030235782 and United States Patent Application No. 20050271974, the contents of which are hereby incorporated herein by reference.

The foregoing description of the invention illustrates and describes the present invention. Additionally, the disclosure shows and describes only certain embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

We claim:

1. A compound of the formula Ai Xi Bi,
where Ai and Bi are each individually an organic onium cation; and
Xi is anion of the formula $^-O_3S-CF_2CF_2OCF_2CF_2-SO_3^-$,
where each of Ai and Bi are selected from

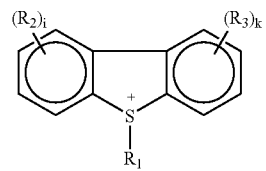

and
Y—Ar
where Ar is selected from

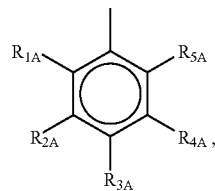

naphthyl, or anthryl;
Y is selected from

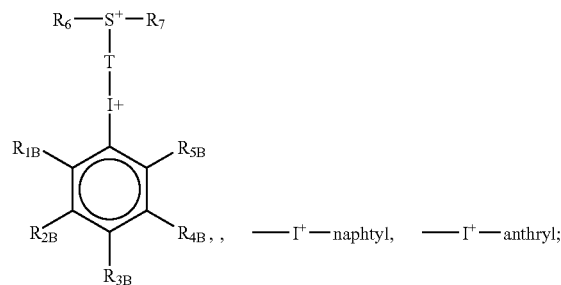

where $R_1$, $R_2$, $R_3$, $R_{1A}$, $R_{1B}$, $R_{2A}$, $R_{2B}$, $R_{3A}$, $R_{3B}$, $R_{4A}$, $R_{4B}$, $R_{5A}$, and $R_{5B}$ are each independently selected from Z, hydrogen, $OSO_2R_9$, $OR_{20}$, straight or branched alkyl chain optionally containing one or more O atoms, monocycloalkyl or polycycloalkyl group optionally containing one or more O atoms, monocycloalkyl- or polycycloalkylcarbonyl group, aryl, aralkyl, arylcarbonylmethyl group, alkoxyalkyl, alkoxycarbonylalkyl, alkylcarbonyl, monocycloalkyl- or polycycloalkyloxycarbonylalkyl with the cycloalkyl ring optionally containing one or more O atoms, monocycloalkyl- or polycycloalkyloxyalkyl with the cycloalkyl ring optionally containing one or more O atoms, straight or branched perfluoroalkyl, monocycloperfluoroalkyl or polycycloperfluoroalkyl, straight or branched alkoxy chain, nitro, cyano, halogen, carboxyl, hydroxyl, sulfate, tresyl, or hydroxyl;

$R_6$ and $R_7$ are each independently selected from straight or branched alkyl chain optionally containing one or more O atoms, monocycloalkyl or polycycloalkyl group optionally containing one or more O atoms, monocycloalkyl- or polycycloalkylcarbonyl group, aryl, aralkyl, straight or branched perfluoroalkyl, monocycloperfluoroalkyl or polycycloperfluoroalkyl, arylcarbonylmethyl group, nitro, cyano, or hydroxyl or $R_6$ and $R_7$ together with the S atom to which they are attached form a 5-, 6-, or 7-membered saturated or unsaturated ring optionally containing one or more O atoms;

R₉ is selected from alkyl, fluoroalkyl, perfluoroalkyl, aryl, fluoroaryl, perfluoroaryl, monocycloalkyl or polycycloalkyl group with the cycloalkyl ring optionally containing one or more O atoms, monocyclofluoroalkyl or polycyclofluoroalkyl group with the cycloalkyl ring optionally containing one or more O atoms, or monocycloperfluoroalkyl or polycycloperfluoroalkyl group with the cycloalkyl ring optionally containing one or more O atoms;

$R_{20}$ is alkoxyalkyl, alkoxycarbonylalkyl, alkylcarbonyl, monocycloalkyl- or polycycloalkyloxycarbonylalkyl with the cycloalkyl ring optionally containing one or more O atoms, or monocycloalkyl- or polycycloalkyloxyalkyl with the cycloalkyl ring optionally containing one or more O atoms;

T is a direct bond, a divalent straight or branched alkyl group optionally containing one or more O atoms, divalent aryl group, divalent aralkyl group, or divalent monocycloalkyl or polycycloalkyl group optionally containing one or more O atoms;

Z is $-(V)_j-(C(X11)(X12))_n-O-C(=O)-R_8$, where either (i) one of X11 or X12 is straight or branched alkyl chain containing at least one fluorine atom and the other is hydrogen, halogen, or straight or branched alkyl chain or (ii) both of X11 and X12 are straight or branched alkyl chain containing at least one fluorine atom;

V is a linkage group selected from a direct bond, a divalent straight or branched alkyl group optionally containing one or more O atoms, divalent aryl group, divalent aralkyl group, or divalent monocycloalkyl or polycycloalkyl group optionally containing one or more O atoms;

X2 is hydrogen, halogen, or straight or branched alkyl chain optionally containing one or more O atoms;

$R_8$ is a straight or branched alkyl chain optionally containing one or more O atoms, a monocycloalkyl or polycycloalkyl group optionally containing one or more O atoms, or aryl;

X3 is hydrogen, straight or branched alkyl chain, halogen, cyano, or $-C(=O)-R_{50}$ where $R_{50}$ is selected from straight or branched alkyl chain optionally containing one or more O atoms or $-O-R_{51}$ where $R_{51}$ is hydrogen or straight or branched alkyl chain;

each of i and k are independently 0 or a positive integer;
j is 0 to 10;
m is 0 to 10;
and n is 0 to 10, the straight or branched alkyl chain optionally containing one or more O atoms, straight or branched alkyl chain, straight or branched alkoxy chain, monocycloalkyl or polycycloalkyl group optionally containing one or more O atoms, monocycloalkyl- or polycycloalkylcarbonyl group, alkoxyalkyl, alkoxycarbonylalkyl, alkylcarbonyl, monocycloalkyl- or polycycloalkyloxycarbonylalkyl with the cycloalkyl ring optionally containing one or more O atoms, monocycloalkyl- or polycycloalkyloxyalkyl with the cycloalkyl ring optionally containing one or more O atoms, aralkyl, aryl, naphthyl, anthryl, 5-, 6-, or 7-membered saturated or unsaturated ring optionally containing one or more O atoms, or arylcarbonylmethyl group being unsubstituted or substituted by one or more groups selected from the group consisting of Z, halogen, alkyl, $C_{1-8}$ perfluoroalkyl, monocycloalkyl or polycycloalkyl, $OR_{20}$, alkoxy, $C_{3-20}$ cyclic alkoxy, dialkylamino, dicyclic dialkylamino, hydroxyl, cyano, nitro, tresyl, oxo, aryl, aralkyl, oxygen atom, $CF_3SO_3$, aryloxy, arylthio, and groups of formulae (II) to (VI):

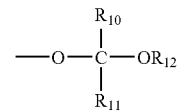

(II)

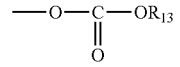

(III)

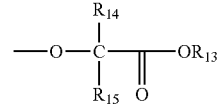

(IV)

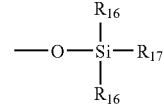

(V)

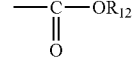

(VI)

wherein $R_{10}$ and $R_{11}$ each independently represent a hydrogen atom, a straight or branched alkyl chain optionally containing one or more O atoms, or a monocycloalkyl or polycycloalkyl group optionally containing one or more O atoms, or $R_{10}$ and $R_{11}$ together can represent an alkylene group to form a five- or six-membered ring;

$R_{12}$ represents a straight or branched alkyl chain optionally containing one or more O atoms, a monocycloalkyl or polycycloalkyl group optionally containing one or more O atoms, or aralkyl, or $R_{10}$ and $R_{12}$ together represent an alkylene group which forms a five- or six-membered ring together with the interposing $-C-O-$ group, the carbon atom in the ring being optionally substituted by an oxygen atom;

$R_{13}$ represents a straight or branched alkyl chain optionally containing one or more O atoms or a monocycloalkyl or polycycloalkyl group optionally containing one or more O atoms;

$R_{14}$ and $R_{15}$ each independently represent a hydrogen atom, a straight or branched alkyl chain optionally containing one or more O atoms or a monocycloalkyl or polycycloalkyl group optionally containing one or more O atoms;

$R_{16}$ represents a straight or branched alkyl chain optionally containing one or more O atoms, a monocycloalkyl or polycycloalkyl group optionally containing one or more O atoms, aryl, or aralkyl; and $R_{17}$ represents straight or branched alkyl chain optionally containing one or more O atoms, a monocycloalkyl or polycycloalkyl group optionally containing one or more O atoms, aryl, aralkyl, the group $-Si(R_{16})_2R_{17}$, or the group $-O-Si(R_{16})_2R_{17}$, the straight or branched alkyl chain optionally containing one or more O atoms, monocycloalkyl or polycycloalkyl group optionally containing one or more O atoms, aryl, and aralkyl being unsubstituted or substituted as above.

2. The compound of claim 1 wherein each of Ai and Bi are selected from

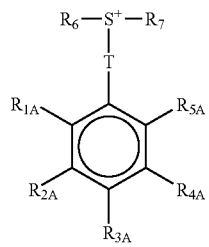 and 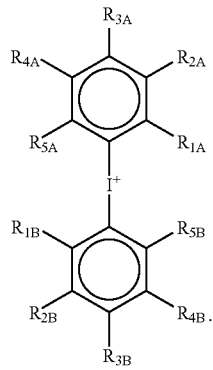

3. The compound of claim 1 where Ai and Bi are each

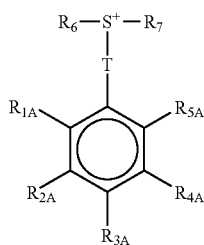

where $R_6$ and $R_7$ are each independently unsubstituted or substituted straight or branched alkyl chain optionally containing one or more O atoms or unsubstituted or substituted aryl, or $R_6$ and $R_7$ together with the S atom to which they are attached form a 5-, 6-, or 7-membered saturated or unsaturated ring optionally containing one or more O atoms; T is a direct bond or a divalent straight or branched alkyl group optionally containing one or more O atoms optionally substituted with oxo.

4. The compound of claim 3 wherein $R_6$ and $R_7$ are each independently unsubstituted or substituted aryl; and T is a direct bond.

5. The compound of claim 4 wherein the aryl of $R_6$ and $R_7$ are each substituted by $OSO_2R_9$, $OR_{20}$, hydroxy, or alkoxy.

6. The compound of claim 3 wherein $R_{3A}$ is selected from hydroxy and straight or branched alkoxy chain and each of $R_{2A}$ and $R_{4A}$ is selected from hydrogen and straight or branched alkyl chain optionally containing one or more O atoms.

7. The compound of claim 3 wherein $R_6$ and $R_7$ together with the S atom to which they are attached form a 5-, 6-, or 7-membered saturated or unsaturated ring optionally containing one or more O atoms; and T is a divalent straight or branched alkyl group optionally containing one or more O atoms optionally substituted with oxo.

8. The compound of claim 1 wherein Ai and Bi are each

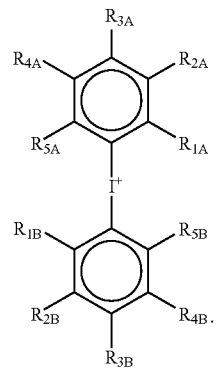

9. The compound of claim 6 wherein each of $R_{3A}$ and $R_{3B}$ is selected from hydrogen, straight or branched alkyl chain optionally containing one or more O atoms, and straight or branched alkoxy chain.

10. The compound of claim 1 selected from the group bis[di(4-t-butyl phenyl) iodonium] di-(tetrafluoroethyl sulfonate) ether, bis[di(4-octyloxyphenyl) iodonium] di-(tetrafluoroethyl sulfonate) ether, bis[(4-octyloxyphenyl)phenyl iodonium] di-(tetrafluoroethyl sulfonate) ether, bis[(4-methylphenyl)phenyl iodonium] di-(tetrafluoroethyl sulfonate) ether, bis[(4-t-butylphenyl)phenyl iodonium] di-(tetrafluoroethyl sulfonate) ether, bis[(4-methoxyphenyl)phenyl iodonium] di-(tetrafluoroethyl sulfonate) ether, bis(4-methoxyphenyl) iodonium di-(tetrafluoroethyl sulfonate) ether, bis (4-octyloxyphenyl)phenyl sulfonium di-(tetrafluoroethyl sulfonate) ether, bis(4-t-butylphenyl diphenyl sulfonium) di-(tetrafluoroethyl sulfonate) ether, bis(4-t-butylphenyl iodonium) di-(tetrafluoroethyl sulfonate) ether, bis(4-t-butylphenyl iodonium) triphenyl sulfonium di-(tetrafluoroethyl sulfonate) ether, bis(benzoyltetramethylenesulfonium) di-(tetrafluoroethyl sulfonate) ether, bis (triphenyl sulfonium) di-(tetrafluoroethyl sulfonate) ether, bis(tris(4-t-butyl phenyl) sulfonium) di-(tetrafluoroethyl sulfonate) ether, bis[bis [2-methyl-adamantylacetyloxymethoxyphenyl]phenylsulfonium] di-(tetrafluoroethyl sulfonate) ether, bis[bis[4-(3,5-di (trifluoromethyl)benzenesulfonyloxy)-phenyl] phenylsulfonium] di-(tetrafluoroethyl sulfonate) ether, bis [bis[4,4-bis(trifluoro-methyl)-3-oxatricyclo[4.2.1.0$^{2,5}$]- nonylmethoxyphenyl]phenyl sulfonium] di-(tetrafluoroethyl sulfonate) ether, and bis[bis[4-pentafluorobenzenesulfonyloxyphenyl]phenylsulfonium] di-(tetrafluoroethyl sulfonate) ether.

11. A photoresist composition useful for imaging in deep UV comprising;
 a) a polymer containing an acid labile group;
 b) a compound of claim 1; and
 c) one or more additional photoacid generators.

12. The composition of claim 11, wherein c) the one or more additional photoacid generators are selected from
 (a) a compound of the formula
 Ai Xi1 Bi, where Ai and Bi are each individually an organic onium cation as previously defined;

Xi1 is an anion of the formula $$Q-R_{500}-SO_3^-$$

where Q is selected from $^-O_3S$ and $^-O_2C$;

$R_{500}$ is a group selected from linear or branched alkyl, cycloalkyl, aryl, or combinations thereof, optionally containing a catenary S or N, where the alkyl, cycloalkyl, and aryl groups are unsubstituted or substituted by one or more groups selected from the group consisting of halogen, unsubstituted or substituted alkyl, unsubstituted or substituted $C_{1-8}$ perfluoroalkyl, hydroxyl, cyano, sulfate, and nitro; and (b) a compound having the formula Ai Xi2, where Ai is an organic onium cation as previously defined and Xi2 is an anion;

and mixtures of (a) and (b) thereof.

13. The composition of claim 12, wherein Xi2 is selected from $CF_3SO_3^-$, $CHF_2SO_3^-$, $CH_3SO_3^-$, $CCl_3SO_3^-$, $C_2F_5SO_3^-$, $C_2HF_4SO_3^-$, $C_4F_9SO_3^-$, camphor sulfonate, perfluorooctane sulfonate, benzene sulfonate, pentafluorobenzene sulfonate, toluene sulfonate, perfluorotoluene sulfonate, $(Rf1SO_2)_3C^-$ and $(Rf1SO_2)_2N^-$, wherein each Rf1 is independently selected from the group consisting of highly fluorinated or perfluorinated alkyl or fluorinated aryl radicals and may be cyclic, when a combination of any two Rf1 groups are linked to form a bridge, further, the Rf1 alkyl chains contain from 1-20 carbon atoms and may be straight, branched, or cyclic, such that divalent oxygen, trivalent nitrogen or hexavalent sulfur may interrupt the skeletal chain, further when Rf1 contains a cyclic structure, such structure has 5 or 6 ring members, optionally, 1 or 2 of which are heteroatoms, and $Rg-O-Rf2-SO_3^-$, where Rf2 is selected from the group consisting of linear or branched $(CF_2)_j$ where j is an integer from 4 to 10 and $C_1$-$C_{12}$ cyclperfluoroalkyl divalent radical which is optionally perfluoro$C_{1-10}$alkyl substituted, Rg is selected from the group consisting of $C_1$-$C_{20}$ linear, branched, monocycloalkyl or polycycloalkyl, $C_1$-$C_{20}$ linear, branched, monocycloalkenyl or polycycloalkenyl, aryl, and aralkyl, the alkyl, alkenyl, aralkyl and aryl groups being unsubstituted, substituted, optionally containing one or more catenary oxygen atoms, partially fluorinated or perfluorinated.

14. The composition of claim 12 wherein the anion Xi2 is selected from include $(C_2F_5SO_2)_2N^-$, $(C_4F_9SO_2)_2N^-$, $(C_8F_{17}SO_2)_3C^-$, $(CF_3SO_2)_3C^-$, $(CF_3SO_2)_2N^-$, $(CF_3SO_2)_2(C_4F_9SO_2)C^-$, $(C_2F_5SO_2)_3C^-$, $(C_4F_9SO_2)_3C^-$, $(CF_3SO_2)_2(C_2F_5SO_2)C^-$, $(C_4F_9SO_2)(C_2F_5SO_2)_2C^-$, $(CF_3SO_2)_2(C_4F_9SO_2)N^-$, $[(CF_3)_2NC_2F_4SO_2]_2N^-$, $(CF_3)_2NC_2F_4SO_2C^-(SO_2CF_3)_2$, $(3,5\text{-bis}(CF_3)C_6H_3)SO_2N^-SO_2CF_3$, $C_6F_5SO_2C^-(SO_2CF_3)_2$, $C_6F_5SO_2N^-SO_2CF_3$,

[Structures: cyclic perfluorinated sulfonimide anions with $SO_2CF_3$ and $C_2F_4SO_2N^-SO_2CF_3$ substituents]

-continued

[Structure: cyclic perfluorinated sulfonimide with $C_2F_4SO_2C^-(SO_2CF_3)_2$]

$CF_3CHFO(CF_2)_4SO_3^-$, $CF_3CH_2O(CF_2)_4SO_3^-$, $CH_3CH_2O(CF_2)_4SO_3$, $CH_3CH_2CH_2O(CF_2)_4SO_3^-$, $CH_3O(CF_2)_4SO_3$, $C_2H_5O(CF_2)_4SO_3$, $C_4H_9O(CF_2)_4SO_3^-$, $C_6H_5CH_2O(CF_2)_4SO_3^-$, $C_2H_5OCF_2CF(CF_3)SO_3^-$, $CH_2=CHCH_2O(CF_2)_4SO_3$, $CH_3OCF_2CF(CF_3)SO_3^-$, $C_4H_9OCF_2CF(CF_3)SO_3^-$, $C_8H_{17}O(CF_2)_2SO_3^-$, and $C_4H_9O(CF_2)_2SO_3^-$.

15. The composition of claim 11, wherein c) the one or more additional photoacid generators are selected from the group bis(4-t-butylphenyl) iodonium triphenyl sulfonium perfluorobutane-1,4-disulfonate, bis(4-t-butylphenyl) iodonium triphenyl sulfonium perfluoropropane-1,3-disulfonate, bis(4-t-butylphenyl) iodonium triphenyl sulfonium perfluoropropane-1-carboxylate-3-sulfonate, bis(4-t-butylphenyl) iodonium triphenyl sulfonium perfluorobutane-1-carboxylate-4-sulfonate, bis(4-t-butylphenyl) iodonium triphenyl sulfonium perfluoromethane disulfonate, bis(4-t-butylphenyl) iodonium triphenyl sulfonium methane disulfonate, bis(4-t-butylphenyl) iodonium triphenyl sulfonium perfluoroethane disulfonate, bis(4-t-butylphenyl) iodonium triphenyl sulfonium ethane disulfonate, bis(triphenyl sulfonium) perfluorobutane-1,4-disulfonate, bis(triphenyl sulfonium) perfluoropropane-1,3-disulfonate, bis(benzoyltetramethylenesulfonium) perfluoropropane-1,3-disulfonate, bis(benzoyltetramethylenesulfonium) perfluorobutane-1,4-disulfonate, bis(tris(4-t-butylphenyl) sulfonium) perfluorobutane-1,4-disulfonate, bis(tris(4-t-butylphenyl) sulfonium) perfluoropropane-1,3-disulfonate, bis(4-t-butylphenyldiphenyl sulfonium) perfluorobutane-1,4-disulfonate, bis(4-t-butylphenyldiphenyl sulfonium) perfluoropropane-1,3-disulfonate, bis(triphenyl sulfonium) perfluoropropane-1-carboxylate-3-sulfonate, bis(triphenyl sulfonium) perfluorobutane-1-carboxylate-4-sulfonate, bis(benzoyltetramethylenesulfonium) perfluoropropane-1-carboxylate-3-sulfonate, bis(benzoyltetramethylenesulfonium) perfluorobutane-1-carboxylate-4-sulfonate, bis(tris(4-t-butyl phenyl) sulfonium) perfluoropropane-1-carboxylate-3-sulfonate, bis(tris(4-t-butyl phenyl) sulfonium) perfluorobutane-1-carboxylate-4-sulfonate, bis(4-t-butylphenyl diphenyl sulfonium) perfluoropropane-1-carboxylate-3-sulfonate, bis(4-t-butylphenyl diphenyl sulfonium) perfluorobutane-1-carboxylate-4-sulfonate, bis(4-t-butylphenyl iodonium) methane disulfonate, bis(triphenyl sulfonium) methane disulfonate, bis(4-t-butylphenyl iodonium) perfluoromethane disulfonate, bis(triphenyl sulfonium) perfluoromethane disulfonate, bis(benzoyltetramethylenesulfonium) perfluoromethane disulfonate, bis(benzoyl-tetramethylenesulfonium) methane disulfonate, bis(tris(4-t-butyl phenyl) sulfonium) perfluoromethane disulfonate, bis(tris(4-t-butyl phenyl) sulfonium) methane disulfonate, bis(4-t-butylphenyl diphenylsulfonium) perfluoromethane disulfonate, bis(4-t-butylphenyl diphenylsulfonium) methane disulfonate, bis(4-octyloxyphenyl) iodonium perfluorobutane-1,4-disulfonate, bis(4-octyloxyphenyl) iodonium ethane disulfonate, bis(4-octyloxyphenyl) iodonium perfluoroethane disulfonate, bis(4-octyloxyphenyl) iodonium perfluoropropane-1,3-disulfonate, bis(4-octyloxyphenyl) iodonium perfluoropropane-1-carboxylate-3-sulfonate, bis(4-octyloxyphenyl) iodonium perfluorobutane-1-carboxylate-4-sulfonate, bis(4-octyloxyphenyl) iodonium methane disulfonate, bis(4-octyloxyphenyl) iodonium perfluoromethane disulfonate, bis(4-octyloxyphenyl)phenyl sulfonium perfluorobutane-1,4-disulfonate, bis(4-octyloxyphenyl)phenyl sulfonium ethane disulfonate, bis(4-octyloxyphenyl)phenyl sulfonium perfluoroethane disulfonate, bis(4-octyloxyphenyl)phenyl sulfonium perfluoropropane-1,3-disulfonate, bis(4-octyloxyphenyl)phenyl sulfonium perfluoropropane-1-carboxylate-3-sulfonate, bis(4-octyloxyphenyl)phenyl sulfonium perfluorobutane-1-carboxylate-4-sulfonate, bis(4-octyloxyphenyl)phenyl sulfonium methane disulfonate, bis(4-octyloxyphenyl)phenyl sulfonium perfluoromethane disulfonate, bis[bis[4-pentafluorobenzenesulfonyloxy-phenyl]phenylsulfonium] perfluorobutane-1,4-disulfonate, bis[bis[4-pentafluoro-benzene-sulfonyloxyphenyl]phenylsulfonium] ethane disulfonate, bis[bis[4-pentafluorobenzenesulfonyloxyphenyl]phenyl-sulfonium] perfluoroethane disulfonate, bis[bis[4-pentafluorobenzene-sulfonyloxyphenyl]phenylsulfonium] perfluoropropane-1,3-disulfonate, bis[bis[4-pentafluorobenzenesulfonyloxyphenyl]phenylsulfonium] perfluoropropane-1-carboxylate-3-sulfonate, bis[bis[4-pentafluorobenzenesulfonyloxy-phenyl]phenylsulfonium] perfluorobutane-1-carboxylate-4-sulfonate, bis[bis[4-pentafluorobenzenesulfonyloxyphenyl]phenylsulfonium] methane disulfonate, bis[bis[4-pentafluorobenzenesulfonyloxyphenyl]phenylsulfonium] perfluoromethane disulfonate, bis[bis[4-(3,5-di(trifluoromethyl)benzenesulfonyloxy)-phenyl]phenylsulfonium] perfluorobutane-1,4-disulfonate, bis[bis[4-(3,5-di(trifluoromethyl)-benzenesulfonyloxy)phenyl]phenylsulfonium]ethane disulfonate, bis[bis[4-(3,5-di(trifluoromethyl)benzenesulfonyloxy)phenyl]phenylsulfonium] perfluoroethane disulfonate, bis[bis[4-(3,5-di(trifluoromethyl)benzenesulfonyloxy)phenyl]phenylsulfonium] perfluoropropane-1,3-disulfonate, bis[bis[4-(3,5-di(trifluoro-methyl)-benzenesulfonyloxy)phenyl]phenylsulfonium] perfluoropropane-1-carboxylate-3-sulfonate, bis[bis[4-(3,5-di(trifluoromethyl)benzenesulfonyloxy)-phenyl]phenylsulfonium] perfluorobutane-1-carboxylate-4-sulfonate, bis[bis[4-(3,5-di(trifluoromethyl)benzenesulfonyloxy)phenyl]phenylsulfonium] methane disulfonate, bis(4-t-butylphenyl iodonium) ethane disulfonate, bis(4-t-butylphenyl iodonium) perfluoroethane disulfonate, bis(triphenyl sulfonium) ethane disulfonate, bis(triphenyl sulfonium) perfluoroethane disulfonate, bis(benzoyltetramethylene-sulfonium) perfluoroethane disulfonate, bis(benzoyltetramethylenesulfonium) ethane disulfonate, bis(tris(4-t-butyl phenyl) sulfonium) perfluoroethane disulfonate, bis(tris(4-t-butyl phenyl) sulfonium) ethane disulfonate, bis(4-t-butylphenyl diphenyl-sulfonium) perfluoroethane disulfonate, bis(4-t-butylphenyl diphenylsulfonium) ethane disulfonate, bis[bis[2-methyladamantylacetyloxymethoxyphenyl]phenyl-sulfonium] perfluorobutane-1,4-disulfonate, bis[bis[2-methyladamantylacetyl-oxymethoxyphenyl]phenylsulfonium]ethane disulfonate, bis[bis[2-methyl-adamantylacetyloxymethoxyphenyl]phenylsulfonium] perfluoroethane disulfonate, bis[bis[2-methyladamantylacetyloxymethoxyphenyl]phenylsulfonium] perfluoro-propane-1,3-disulfonate, bis[bis[2-methyladamantylacetyloxymethoxyphenyl]phenylsulfonium] perfluoropropane-1-carboxylate-3-sulfonate, bis[bis[2-methyl-adamantylacetyloxymethoxyphenyl]phenylsulfonium] perfluorobutane-1-carboxylate-4-sulfonate, bis[bis[2-methyladamantylacetyloxymethoxyphenyl]phenylsulfonium] methane disulfonate, bis[bis[2-methyladamantylacetyloxymethoxyphenyl]phenylsulfonium] perfluoromethane disulfonate, bis[bis[4,4-bis(trifluoromethyl)-3-oxatricyclo[4.2.1.0$^{2,5}$]-nonylmethoxyphenyl]phenyl sulfonium] perfluorobutane-1,4-disulfonate, bis[bis[4,4-bis(trifluoromethyl)-3-oxatricyclo-[4.2.1.0$^{2,5}$]-nonylmethoxy-phenyl]phenyl sulfonium]ethane disulfonate, bis[bis[4,4-bis(trifluoromethyl)-3-oxatricyclo[4.2.1.0$^{2,5}$]-nonylmethoxyphenyl] phenyl sulfonium]-perfluoroethane disulfonate, bis[bis[4,4-bis(trifluoromethyl)-3-oxatricyclo[4.2.1.0$^{2,5}$]-nonylmethoxy-phenyl]phenyl sulfonium]perfluoropropane-1,3-disulfonate, bis[bis[4,4-bis(trifluoro-methyl)-3-oxatricyclo[4.2.1.0$^{2,5}$]-nonylmethoxyphenyl]phenyl sulfonium]-perfluoropropane-1-carboxylate-3-sulfonate, bis[bis[4,4-bis(trifluoro-methyl)-3-oxatricyclo[4.2.1.0$^{2,5}$]-nonylmethoxyphenyl]phenyl sulfonium]perfluoro-butane-1-carboxylate-4-sulfonate, bis[bis[4,4-bis(trifluoromethyl)-3-oxatricyclo-[4.2.1.0$^{2,5}$]-nonylmethoxyphenyl]phenyl sulfonium]methane disulfonate, bis[bis[4,4-bis(trifluoromethyl)-3-oxatricyclo[4.2.1.0$^{2,5}$]-nonylmethoxyphenyl]phenyl sulfonium] perfluoromethane disulfonate, bis(4-t-butylphenyl) iodonium bis-perfluoroethane sulfonimide, diphenyliodonium trifluoromethane sulfonate, diphenyliodonium nonafluorobutane sulfonate, triphenylsulfonium trifluoromethane sulfonate, triphenylsulfonium nonafluorobutane sulfonate, 4-(1-butoxyphenyl)diphenylsulfonium bis-(perfluorobutanesulfonyl)imide, 4-(1-butoxyphenyl) diphenylsulfonium bis-(perfluoroethanesulfonyl)imide, 2,4,6-trimethylphenyldiphenylsulfonium bis-perfluorobutanesulfonyl)imide, 2,4,6-trimethylphenyldiphenylsulfonium bis-(perfluoroethanesulfonyl)imide, toluenediphenylsulfonium bis-(perfluorobutanesulfonyl)imide, toluenediphenylsulfonium bis-(perfluoroethanesulfonyl)imide, toluenediphenylsulfonium-(trifluoromethyl perfluorobutylsulfonyl)imide, tris-(tert-butylphenyl)sulfonium-(trifluoromethyl perfluorobutylsulfonyl)imide, tris-(tert-butylphenyl)sulfonium bis-(perfluorobutanesulfonyl)imide, tris-(tert-butylphenyl)sulfonium-bis-(trifluoromethanesulfonyl)imide, and mixtures thereof.

16. The composition of claim 11, wherein b) the compound of claim 1 is selected from the group bis[di(4-t-butyl phenyl) iodonium] di-(tetrafluoroethyl sulfonate) ether, bis[di(4-octyloxyphenyl) iodonium] di-(tetrafluoroethyl sulfonate) ether, bis[(4-octyloxyphenyl)phenyl iodonium] di-(tetrafluoroethyl sulfonate) ether, bis[(4-methylphenyl)phenyl iodonium] di-(tetrafluoroethyl sulfonate) ether, bis[(4-t-butylphenyl)phenyl iodonium] di-(tetrafluoroethyl sulfonate) ether, bis[(4-methoxyphenyl)phenyl iodonium] di-(tetrafluoroethyl sulfonate) ether, bis(4-methoxyphenyl) iodonium di-(tetrafluoroethyl sulfonate) ether, bis(4-octyloxyphenyl)phenyl sulfonium di-(tetrafluoroethyl sulfonate) ether, bis(4-t-butylphenyl diphenyl sulfonium) di-(tetrafluoroethyl sulfonate) ether, bis(4-t-butylphenyl iodonium) di-(tetrafluoroethyl sulfonate) ether, bis(4-t-butylphenyl iodonium) triphenyl sulfonium di-(tetrafluoroethyl sulfonate) ether, bis(benzoyltetramethylenesulfonium) di-(tetrafluoroethyl sulfonate) ether, bis(triphenyl sulfonium) di-(tetrafluoroethyl sulfonate) ether, bis(tris(4-t-butyl phenyl) sulfonium) di-(tetrafluoroethyl sulfonate) ether, bis[bis[2-methyl-adamantylacetyloxymethoxyphenyl]phenylsulfonium] di-(tetrafluoroethyl sulfonate) ether, bis[bis[4-(3,5-di(trifluoromethyl)benzenesulfonyloxy)-phenyl]phenylsulfonium] di-(tetrafluoroethyl sulfonate) ether, bis[bis[4,4-bis(trifluoro-methyl)-3-oxatricyclo[4.2.1.0$^{2,5}$]-nonylmethoxyphenyl]phenyl sulfonium] di-(tetrafluoroethyl sulfonate) ether, and bis [bis[4-pentafluorobenzenesulfonyloxyphenyl]phenylsulfonium] di-(tetrafluoroethyl sulfonate) ether, and mixtures thereof.

17. The composition of claim 11, wherein the ratio of b) to c) ranges from about 1:1 to about 1:4.

18. The composition of claim 11, wherein the ratio of b) to c) ranges from about 1:1.25 to about 1:3.5.

19. A process for imaging a photoresist comprising the steps of: include
- a) applying a coating layer a substrate with the composition of claim 11;
- b) baking the substrate to substantially remove the solvent;
- c) image-wise exposing the photoresist coating;
- d) optionally, postexposure baking the photoresist coating; and
- e) developing the photoresist coating with an aqueous alkaline solution.

20. A coated substrate comprising a substrate with a photoresist coating film, wherein the photoresist coating film is formed from the photoresist composition of claim 11.

* * * * *